US005635352A

United States Patent [19]
Urdea et al.

[11] Patent Number: 5,635,352
[45] Date of Patent: Jun. 3, 1997

[54] SOLUTION PHASE NUCLEIC ACID SANDWICH ASSAYS HAVING REDUCED BACKGROUND NOISE

[75] Inventors: Michael S. Urdea, Alamo; Timothy Fultz; Brian D. Warner, both of Martinez; Mark Collins, Walnut Creek, all of Calif.

[73] Assignee: Chiron Corporation, Emeryville, Calif.

[21] Appl. No.: 429,181

[22] Filed: Apr. 26, 1995

Related U.S. Application Data

[63] Continuation of Ser. No. 164,388, Dec. 8, 1993.

[51] Int. Cl.$^6$ ........................ C12Q 1/68
[52] U.S. Cl. ............... 435/6; 435/91.1; 435/808; 435/810; 436/501; 536/22.1; 536/23.1; 536/24.1; 536/24.3; 536/24.31; 536/24.32; 536/24.33; 935/77; 935/78
[58] Field of Search ................ 435/6, 91.1, 808, 435/810; 436/501; 536/22.1, 23.1, 24.1, 24.3–0.33; 935/77, 78

[56] References Cited

U.S. PATENT DOCUMENTS

| | | | |
|---|---|---|---|
| 4,868,105 | 9/1989 | Urdea et al. | 435/6 |
| 4,894,325 | 1/1990 | Englehardt et al. | 435/6 |
| 5,124,246 | 6/1992 | Urdea et al. | 435/6 |
| 5,175,270 | 12/1992 | Nilsen et al. | 536/27 |
| 5,424,413 | 6/1995 | Hogan et al. | 536/24.31 |
| 5,451,503 | 9/1995 | Hogan et al. | 435/6 |
| 5,457,025 | 10/1995 | Collins et al. | 435/6 |

FOREIGN PATENT DOCUMENTS

| | | |
|---|---|---|
| 0 070685 | 1/1983 | European Pat. Off. . |
| 0 361983 | 4/1990 | European Pat. Off. . |
| 0 469 755 A1 | 2/1992 | European Pat. Off. . |
| 0 552 931 A1 | 7/1993 | European Pat. Off. . |
| WO 93/13221 | 7/1993 | WIPO . |
| WO 93/13223 | 7/1993 | WIPO . |
| WO 93/13227 | 7/1993 | WIPO . |

OTHER PUBLICATIONS

Horne et al., "Recognition of Mixed–Sequence Duplex DNA by Alternate–Strand Triple–Helix Formation", *J. Am. Chem. Soc.* 112:2435–2437 (1989).

Distefano et al., "Ligand–Promoted Dimerization of Oligonucleotides Binding Cooperatively to DNA", *J. Am. Chem. Soc.* 114:11006–11007 (1992).

*Primary Examiner*—Ardin H. Marschel
*Attorney, Agent, or Firm*—Reed & Robins; Kenneth M. Goldman; Robert P. Blackburn

[57] ABSTRACT

New techniques are provided for substantially reducing background signals encountered in solution phase hybridization assays. The techniques are premised on eliminating or significantly reducing the phenomena of nonspecific hybridization and nonspecific binding, so as to provide a detectable signal which is produced only in the presence of the target polynucleotide of interest. In certain embodiments, methods are provided for increasing the signal which can otherwise be diminished in noise reduction. Kits for carrying out the novel assays are provided as well.

25 Claims, 13 Drawing Sheets

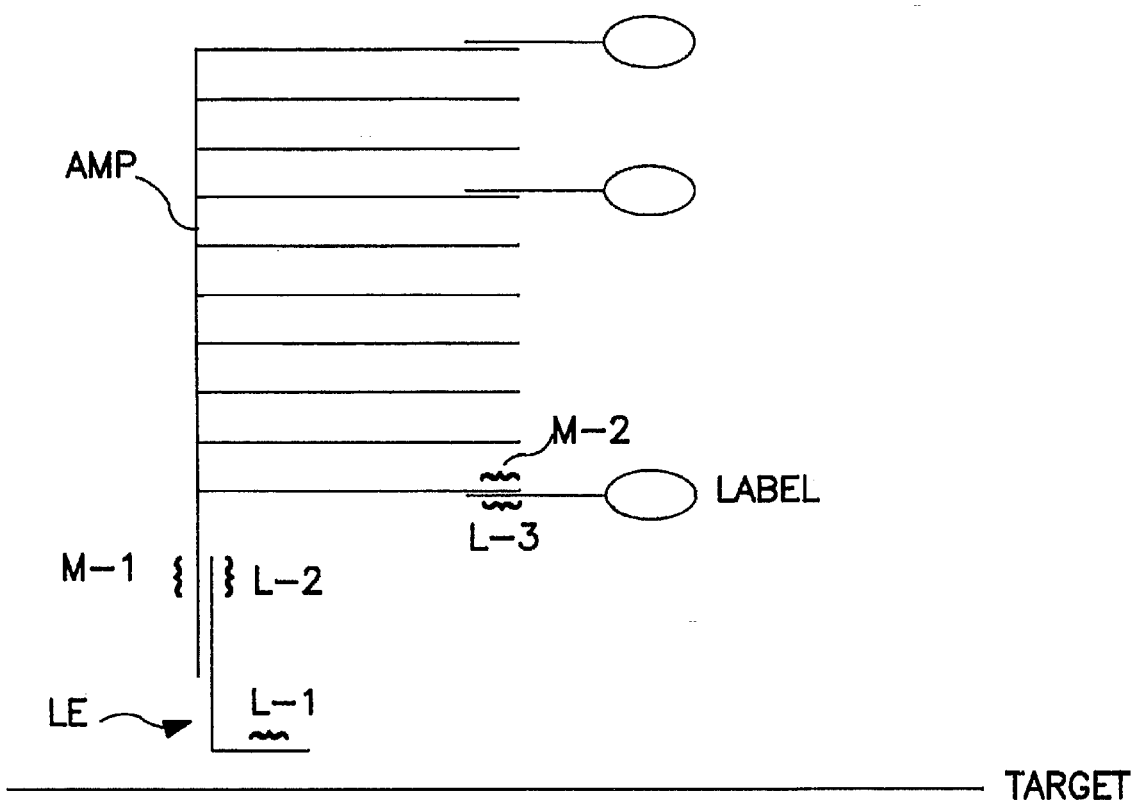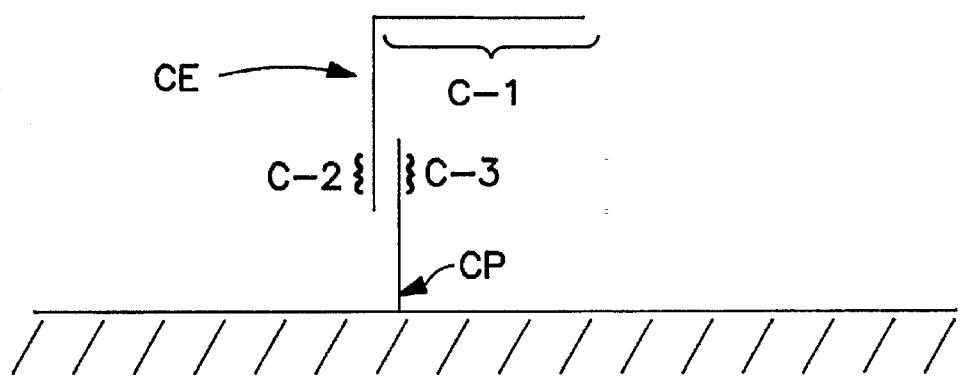
FIG. 1

SOLID SUPPORT

SOLID SUPPORT

SEQUENCE LISTING ( 1 ) GENERAL INFORMATION:

( i i i ) NUMBER OF SEQUENCES: 61

( 2 ) INFORMATION FOR SEQ ID NO:1:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
TTTCAGCAAT  CAGGTGTTCT  CGTCCTGGCA  ATTCCGGTGT  ACTCACCGGT  TC          52
```

( 2 ) INFORMATION FOR SEQ ID NO:2:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
TTTCAGCAAT  CAGGTGTTCT  CWTTCCGGCG  ATTCCGGTGT  ACTCACCGGT  TC          52
```

( 2 ) INFORMATION FOR SEQ ID NO:3:

( i ) SEQUENCE CHARACTERISTICS:
        ( A ) LENGTH: 46 base pairs
        ( B ) TYPE: nucleic acid (C) STRANDEDNESS: single
(D) TOPOLOGY: linear (ii) MOLECULE TYPE: DNA (genomic)

(xi) SEQUENCE DESCRIPTION: SEQ ID NO:3:

GTATTGAGCG GGTTKMTCCA AGAAAGGACC CGGTCGGCTC TGGGAC 46

(2) INFORMATION FOR SEQ ID NO:4:

(i) SEQUENCE CHARACTERISTICS:
(A) LENGTH: 46 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:4:

GCATAGAGTG GGTTWATCCA AGAAAGGACC CAGTCGGCTC TGGGAC 46

(2) INFORMATION FOR SEQ ID NO:5:

(i) SEQUENCE CHARACTERISTICS:
(A) LENGTH: 52 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:5:

TTTCAGCAAT CAGGTGTTCA GCAGTCTTGC GGGGGCACGC CCAAATCTCC AG 52

(2) INFORMATION FOR SEQ ID NO:6:

(i) SEQUENCE CHARACTERISTICS:
(A) LENGTH: 52 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:6:

TTTCAGCAAT CAGGTGTTCA GTGATCTTGC GGGGGCGTGC CCAAATCTCC AG 52

(2) INFORMATION FOR SEQ ID NO:7:

(i) SEQUENCE CHARACTERISTICS:
(A) LENGTH: 52 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:7:

TTTCAGCAAT CAGGTGTTCA GCAGTCTCGC GGGGGCACGC CCAAATCTCC AG 52

(2) INFORMATION FOR SEQ ID NO:8:

(i) SEQUENCE CHARACTERISTICS:
(A) LENGTH: 52 base pairs
(B) TYPE: nucleic acid
(C) STRANDEDNESS: single
(D) TOPOLOGY: linear (ii) MOLECULE TYPE: DNA (genomic)

( x i ) SEQUENCE DESCRIPTION: SEQ ID NO:8:

TTTCAGCAAT CAGGTGTTCA GCAGTCTTGC GGGGGCACGC CCAAATGGCT GG    52

( 2 ) INFORMATION FOR SEQ ID NO:9:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

TTTCAGCAAT CAGGTGTTCA GTGATCTCGC GGGGGCACGC CCAAATTTCT GG    52

( 2 ) INFORMATION FOR SEQ ID NO:10:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

ACAAGGCCTT TCGCGACCCA ACACTACTCG GCTTCGGCTC TGGGAC    46

( 2 ) INFORMATION FOR SEQ ID NO:11:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

ACAAGGCCKT TCGCAACCCA ACGCTACTMG GCTTCGGCTC TGGGAC    46

( 2 ) INFORMATION FOR SEQ ID NO:12:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

AGGCATAGGA CCCGTGTCTT TCCTCACAGG GGAGTGATTC ATGGTGGAGT GTC    53

( 2 ) INFORMATION FOR SEQ ID NO:13:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

AGGCATAGGA CCCGTGTCTT ATGGCTAGGC GCTTTCTGCG TGAAGACAGT AGT    53

( 2 ) INFORMATION FOR SEQ ID NO:14:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

```
AGGCATAGGA  CCCGTGTCTT  KCCTGGAGGC  TGTACGASAC  TSGTACTAGC  GCC         53
```

( 2 ) INFORMATION FOR SEQ ID NO:15:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

```
AGGCATAGGA  CCCGTGTCTT  CGCAGACCAC  TATGGCTCTC  CCGGGAGGGG  GGG         53
```

( 2 ) INFORMATION FOR SEQ ID NO:16:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

```
AGGCATAGGA  CCCGTGTCTT  GGGGCACTCG  CAAGCACCCT  ATCAGGCAGT  ACC         53
```

( 2 ) INFORMATION FOR SEQ ID NO:17:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

```
AGGCATAGGA  CCCGTGTCTT  TGTGCTCATG  KTGCACGGTC  TACGAGACCT  CCC         53
```

( 2 ) INFORMATION FOR SEQ ID NO:18:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

```
TCGGCTCTGG  GAC                                                        13
```

( 2 ) INFORMATION FOR SEQ ID NO:19:

( i ) SEQUENCE CHARACTERISTICS:
        ( A ) LENGTH: 16 base pairs
        ( B ) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO:19:

CAGCAATCAG GTGTTC                                                                                           16

( 2 ) INFORMATION FOR SEQ ID NO:20:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: misc_feature
( B ) LOCATION: 1..2
( D ) OTHER INFORMATION: /note= "N is
( N 4 - ( 6- aminocaproyl-2-aminoethyl)-5-methylcytidine)"

( x i ) SEQUENCE DESCRIPTION: SEQ ID NO:20:

NGTCCCAGAG CCGAGAACAC CTGATTGCTG                                                                            30

( 2 ) INFORMATION FOR SEQ ID NO:21:

( i ) SEQUENCE CHARACTERISTICS:
( A ) LENGTH: 60 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:21:

GATGTGGTTG TCGTACTTGA TGTGGTTGTC GTACTTGATG TGGTTGTCGT ACTTGCGTAG         60

( 2 ) INFORMATION FOR SEQ ID NO:22:

( i ) SEQUENCE CHARACTERISTICS:
( A ) LENGTH: 12 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:22:

CAGTCACTAC GC                                                                                               12

( 2 ) INFORMATION FOR SEQ ID NO:23:

( i ) SEQUENCE CHARACTERISTICS:
( A ) LENGTH: 55 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:23:

TCCTCACAGG GGAGTGATTC ATGGTGGAGT GTCCTCTTGG AAAGAAAGTG AAGTG             55

( 2 ) INFORMATION FOR SEQ ID NO:24:

( i ) SEQUENCE CHARACTERISTICS:
( A ) LENGTH: 55 base pairs ( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:24:

ATGGCTAGAC GCTTTCTGCG TGAAGACAGT AGTCTCTTGG AAAGAAAGTG AAGTG    55

( 2 ) INFORMATION FOR SEQ ID NO:25:

( i ) SEQUENCE CHARACTERISTICS:
( A ) LENGTH: 55 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:25:

TCCTGGAGGC TGCACGACRC TCATACTAAC GCCCTCTTGG AAAGAAAGTG AAGTG    55

( 2 ) INFORMATION FOR SEQ ID NO:26:

( i ) SEQUENCE CHARACTERISTICS:
( A ) LENGTH: 55 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:26:

CGCAGACCAC TATGGCTCT Y CCGGGAGGGG GGGCTCTTGG AAAGAAAGTG AAGTG    55

( 2 ) INFORMATION FOR SEQ ID NO:27:

( i ) SEQUENCE CHARACTERISTICS:
( A ) LENGTH: 55 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:27:

TCRTCC Y GGC AATTCCGGTG TACTCACCGG TTCCTCTTGG AAAGAAAGTG AAGTG    55

( 2 ) INFORMATION FOR SEQ ID NO:28:

( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:28:

CTGAGTTTCT GGCTCGCATT GAGCGGGTTD ATCCAAGAAA GGACCCGG    48

( 2 ) INFORMATION FOR SEQ ID NO:29:

( i ) SEQUENCE CHARACTERISTICS:
( A ) LENGTH: 64 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:29:

ACTGAGTCAG TCAGTCAGCA GTCT Y GCGGG GGCACGCCCA ARTCTCCAGG AAAGTTTGAA 60

TATG 64

( 2 ) INFORMATION FOR SEQ ID NO:30:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

CTGAGTTTCT GGCTCACAAG GCCTTTCGCA ACCCAACACT ACTCGGCTAC CTACCTACCT 60

ACCT 64

( 2 ) INFORMATION FOR SEQ ID NO:31:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

AGTCAGTCAG TCAGTCGGGG CACTCGCAAG CACCCTATCA GGCAGTACCG AAAGTTTGAA 60

TATG 64

( 2 ) INFORMATION FOR SEQ ID NO:32:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:32:

CTGAGTTTCT GGCTC Y GTGC TCATGRTGCA CGGTCTACGA GACCTCCCAC CTACCTACCT 60

ACCT 64

( 2 ) INFORMATION FOR SEQ ID NO:33:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:33:

AGTCAGTCAG TCAGTCGTTA CGTTTGKTT Y TT Y TTTGRGG TTTRGGAWTG AAAGTTTGAA 60

TATG 64

( 2 ) INFORMATION FOR SEQ ID NO:34:

( i ) SEQUENCE CHARACTERISTICS:
        ( A ) LENGTH: 49 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:34:

CGGGAACTTR ACGTCCTGTG GGCGRCGGTT GGTACCTACC TACCTACCT          49

(2) INFORMATION FOR SEQ ID NO:35:

(i) SEQUENCE CHARACTERISTICS:
(A) LENGTH: 53 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:35:

AGGCATAGGA CCCGTGTCTT CARGTAAACT CCACCRACGA TCTGRCCRCC RCC     53

(2) INFORMATION FOR SEQ ID NO:36:

(i) SEQUENCE CHARACTERISTICS:
(A) LENGTH: 53 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:36:

AGGCATAGGA CCCGTGTCTT RCGCACACCC AAYCTRGGGC CCCTGCGCGG CAA     53

(2) INFORMATION FOR SEQ ID NO:37:

(i) SEQUENCE CHARACTERISTICS:
(A) LENGTH: 53 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:37:

AGGCATAGGA CCCGTGTCTT AGGTTGCGAC CGCTCGGAAG TCTTYCTRGT CGC     53

(2) INFORMATION FOR SEQ ID NO:38:

(i) SEQUENCE CHARACTERISTICS:
(A) LENGTH: 53 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:38:

AGGCATAGGA CCCGTGTCTT RCGHRCCTTG GGGATAGGCT GACGTCWACC TCG     53

(2) INFORMATION FOR SEQ ID NO:39:

(i) SEQUENCE CHARACTERISTICS:
(A) LENGTH: 53 base pairs
(B) TYPE: nucleic acid
(C) STRANDEDNESS: single
(D) TOPOLOGY: linear (ii) MOLECULE TYPE: DNA (genomic)

( x i ) SEQUENCE DESCRIPTION: SEQ ID NO:39:

AGGCATAGGA CCCGTGTCTT RCGHRCCTTG GGGATAGGTT GTCGCCWTCC ACG     53

( 2 ) INFORMATION FOR SEQ ID NO:40:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:40:

AGGCATAGGA CCCGTGTCTT Y CCRGGCT-
GR GCCCAGR Y CC TRCCCTCGGR Y Y G     53

( 2 ) INFORMATION FOR SEQ ID NO:41:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:41:

AGGCATAGGA CCCGTGTCTT BSHRCCCTCR TTRCCRTAGA GGGGCCADGG RTA     53

( 2 ) INFORMATION FOR SEQ ID NO:42:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:42:

AGGCATAGGA CCCGTGTCTT GCCRGGGGW GACAGGAGCC ATCC Y GCCCA CCC     53

( 2 ) INFORMATION FOR SEQ ID NO:43:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:43:

AGGCATAGGA CCCGTGTCTT CCGGGGGTC Y GTGGGGCCCC A Y CTAGGCCG RGA     53

( 2 ) INFORMATION FOR SEQ ID NO:44:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:44:

AGGCATAGGA CCCGTGTCTT ATCGATGACC TTACCCAART TRCGCGACCT RCG     53

( 2 ) INFORMATION FOR SEQ ID NO:45:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:45:

AGGCATAGGA CCCGTGTCTT CCCCATGAGR TCGGCGAAGC CGCA Y GTRAG GGT    53

( 2 ) INFORMATION FOR SEQ ID NO:46:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:46:

AGGCATAGGA CCCGTGTCTT GCATTGAGCG GGTTDATCCA AGAAAGGACC CGG    53

( 2 ) INFORMATION FOR SEQ ID NO:47:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:47:

AGGCATAGGA CCCGTGTCTT AGCAGTCT Y G CGGGGGCACG CCCAARTCTC CAG    53

( 2 ) INFORMATION FOR SEQ ID NO:48:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:48:

AGGCATAGGA CCCGTGTCTT ACAAGGCCTT TCGCAACCCA ACACTACTCG GCT    53

( 2 ) INFORMATION FOR SEQ ID NO:49:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:49:

AGGCATAGGA CCCGTGTCTT GGGGCACTCG CAAGCACCCT ATCAGGCAGT ACC    53

( 2 ) INFORMATION FOR SEQ ID NO:50:

( i ) SEQUENCE CHARACTERISTICS:

(A) LENGTH: 53 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:50:

| AGGCATAGGA | CCCGTGTCTT | YGTGCTCATG | RTGCACGGTC | TACGAGACCT | CCC | 53 |

(2) INFORMATION FOR SEQ ID NO:51:

(i) SEQUENCE CHARACTERISTICS:
(A) LENGTH: 53 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:51:

| AGGCATAGGA | CCCGTGTCTT | GTTACGTTTG | KTTYTTYTTT | GRGGTTTRGG | AWT | 53 |

(2) INFORMATION FOR SEQ ID NO:52:

(i) SEQUENCE CHARACTERISTICS:
(A) LENGTH: 53 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:52:

| AGGCATAGGA | CCCGTGTCTT | CGGGAACTTR | ACGTCCTGTG | GGCGRCGGTT | GGT | 53 |

(2) INFORMATION FOR SEQ ID NO:53:

(i) SEQUENCE CHARACTERISTICS:
(A) LENGTH: 235 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:53:

| AGGCATAGGA | CCCGTGTCTT | TTTTAGGCAT | AGGACCCGTG | TCTTTTTTAG | GCATAGGACC | 60 |
| CGTGTCCGTG | GATGTTTGAG | GCATAGGACC | CGTGTCTTTT | TTAGGCATAG | GACCCGTGTC | 120 |
| TTTTTAGGC | ATAGGACCCG | TGTCGCGTAG | TGACTGAGGC | ATAGGACCCG | TGTCTTTTTT | 180 |
| AGGCATAGGA | CCCGTGTCTT | TTTTCATATT | CAAACTTTCG | AGCCAGAAAC | TCAGT | 235 |

(2) INFORMATION FOR SEQ ID NO:54:

(i) SEQUENCE CHARACTERISTICS:
(A) LENGTH: 182 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:54:

| AGGCATAGGA | CCCGTGTCTT | TTTTAGGCAT | AGGACCCGTG | TCTTTTTTAG | GCATAGGACC | 60 |
| CGTGTCCGTG | GATGTTTGAG | GCATAGGACC | CGTGTCTTTT | TTAGGCATAG | GACCCGTGTC | 120 |

TTTTTAGGC ATAGGACCCG TGTCTTTTTT AGGTAGGTAG GTAGGTGACT GACTGACTGA    180
CT    182

( 2 ) INFORMATION FOR SEQ ID NO:55:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..2
        ( D ) OTHER INFORMATION: /note= "N is
        ( N 4 - ( 6- aminocaproyl-2-aminoethyl)-5-methylcytidine)"

( x i ) SEQUENCE DESCRIPTION: SEQ ID NO:55:

NCACTTCACT TTCTTTCCAA GAG    23

( 2 ) INFORMATION FOR SEQ ID NO:56:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:56:

TCCTCACAGG GGAGTGATTC ATGGTGGAGT GTCCTTCTTT GGAGAAAGTG GTG    53

( 2 ) INFORMATION FOR SEQ ID NO:57:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:57:

ATGGCTAGAC GCTTTCTGCG TGAAGACAGT AGTCTTCTTT GGAGAAAGTG GTG    53

( 2 ) INFORMATION FOR SEQ ID NO:58:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:58:

GCCTGGAGGC TGCACGRCAC TCATACTAAC GCCCTTCTTT GGAGAAAGTG GTG    53

( 2 ) INFORMATION FOR SEQ ID NO:59:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: DNA (genomic)

(x i) SEQUENCE DESCRIPTION: SEQ ID NO:59:

CGCAGACCAC TATGGCTCT Y CCGGGAGGGG GGGCTTCTTT GGAGAAAGTG GTG    53

(2) INFORMATION FOR SEQ ID NO:60:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:60:

TCRTCC Y GGC AATTCCGGTG TACTCACCGG TTCCTTCTTT GGAGAAAGTG GTG    53

(2) INFORMATION FOR SEQ ID NO:61:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:61:

CACCACTTTC TCCAAAGAAG    20

SOLUTION PHASE NUCLEIC ACID SANDWICH ASSAYS HAVING REDUCED BACKGROUND NOISE

This application is a continuation of application Ser. No. 08/164,388, filed 8 Dec. 1993.

TECHNICAL FIELD

This invention relates generally to nucleic acid chemistry and hybridization assays. More particularly, the invention relates to methods for generating a more target-dependent signal in solution phase sandwich hybridization assays by minimizing background noise deriving primarily from nonspecific hybridization and/or nonspecific binding. The invention additionally relates to methods for compensating for lost signal while reducing background noise. The invention further relates to kits containing the reagents necessary for carrying out the disclosed assays.

BACKGROUND

Nucleic acid hybridization assays are commonly used in genetic research, biomedical research and clinical diagnostics. In a basic nucleic acid hybridization assay, single-stranded analyte nucleic acid is hybridized to a labeled single-stranded nucleic acid probe and resulting labeled duplexes are detected. Variations of this basic scheme have been developed to enhance accuracy, facilitate the separation of the duplexes to be detected from extraneous materials, and/or amplify the signal that is detected.

The present invention is directed to a method of reducing background signals encountered in solution phase sandwich hybridization assays that derive from several sources. Generally, the background noise which is addressed by way of the presently disclosed techniques results from undesirable interaction of various polynucleotide components that are used in a given assay, i.e., interaction which gives rise to a signal which does not correspond to the presence or quantity of analyte. The invention is useful in conjunction with any number of assay formats wherein multiple hybridization steps are carried out to produce a detectable signal which correlates with the presence or quantity of a polynucleotide analyte.

One such assay is described in detail in commonly assigned U.S. Pat. No. 4,868,105 to Urdea et al. That assay involves the use of a two-part capturing system designed to bind the polynucleotide analyte to a solid support, and a two-part labeling system designed to bind a detectable label to the polynucleotide analyte to be detected or quantitated. The two-part capture system involves the use of capture probes bound to a solid support and capture extender molecules which hybridize both to a segment of the capture probes and to a segment of the polynucleotide analyte. The two-part labelling system involves the use of label probe extender molecules which hybridize to a segment of the polynucleotide analyte, and label probes which hybridize to the label probe extender molecules and contain or bind to a detectable label. An advantage of such a system is that a plurality of hybridization steps must occur in order for label to be detected in a manner that correlates with the presence of the analyte, insofar as two distinct hybridization reactions must occur for analyte "capture," and, similarly, two distinct hybridization reactions must occur for analyte labelling. However, there remain a number of ways in which a detectable signal can be generated in a manner which does not correspond to the presence or quantity of analyte, and these will be discussed in detail below.

Another example of an assay with which the present invention is useful is a signal amplification method which is described in commonly assigned U.S. Pat. No. 5,124,246 to Urdea et al. In that method, the signal is amplified through the use of amplification multimers, polynucleotides which are constructed so as to contain a first segment that hybridizes specifically to the analyte nucleic acid or a strand of nucleic acid bound to the analyte, and a multiplicity of second segments that hybridize specifically to a labeled probe. The degree of amplification is theoretically proportional to the number of iterations of the second segment. The multimers may be either linear or branched. Branched multimers may be in the shape of a fork or a comb, with comb-type multimers preferred.

One approach which has been proposed to increase the target dependence of the signal in a hybridization assay is described in European Patent Publication No. 70,685, inventors M. J. Heller et al. That reference describes a homogeneous hybridization assay in which a nonradiative transfer of energy occurs between proximal probes; two distinct events must occur for a target-generated signal to be produced, enhancing the accuracy of detection. A second approach designed to enhance the signal deriving from the presence of analyte is described in European Patent Publication No. 361,983 inventor J. E. Stefano. The method described therein involves hybridization of two probe sequences (one a midivariant RNA (MDV), the other a half-ribozyme), each of which is complementary to sequences present in an RNA target. The ribozyme thus formed specifically cleaves the tail of the MDV probe, releasing the MDV probe from the support and enhancing its replication. Still a third approach to increase specificity in hybridization assays is described by Distefano et al., *J. Am Chem. Soc.* (1992) 114:11006–11007. That method involves the use of short regions of double-helix formation to enhance the stability of two short regions of triple-helix DNA.

European Patent Publication No. 552,931, inventors Hogan et al., describe a nucleic acid hybridization assay utilizing a probe system that detects regions of double-stranded DNA that only form in the presence of target sequence.

The present invention, which does not rely on the detection of the presence of double-stranded regions, is also designed to increase the accuracy of detection and quantitation of polynucleotide analytes in hybridization assays. The invention increases both the sensitivity and specificity of such assays, by reducing the incidence of signal generation that occurs in the absence of target, and does not involve a substantial increase in either time or cost relative to current assay configurations. In certain embodiments, the invention is also effective in compensating for the loss in signal that can result when background noise is reduced.

SUMMARY OF THE INVENTION

Methods and kits are provided for detecting nucleic acid analytes in a sample. In general, the methods represent improvements on solution phase sandwich hybridization which involve binding the analyte to a solid support, labelling the analyte, and detecting the presence of label on the support. Preferred methods involve the use of amplification multimers which enable the binding of significantly more label in the analyte-probe complex, enhancing assay sensitivity and specificity.

In a first aspect of the invention, an assay is provided in which two or more distinct "capture extender" molecules are used, each of which must bind to the analyte in order for the assay to result in a detectable signal. As noted above, capture extender molecules are bridging probes which bind to the analyte as well as to support bound "capture probes." In one embodiment, at least two capture extender molecules must bind to a single support-bound capture probe in order for the assay to result in a detectable signal.

In a further, related aspect of the invention, an assay is provided in which the melt temperature $T_{m1}$ of the multi-component complex formed between the analyte and support-bound capture probes, mediated by two or more distinct capture extender molecules, is significantly higher than the melt temperature $T_{m2}$ of each two-component complex formed between a capture probe and an individual capture extender molecule. In this aspect, the assay is carried out at conditions which favor formation of hybrid complexes in which analyte molecule is bound to the capture probes. This technique is premised on the enhanced stability of the multi-component complex relative to the less stable two-component complexes. A preferred method of favoring analyte-bound hybrid complexes includes running one or more steps of the assay at a temperature between $T_{m1}$ and $T_{m2}$.

In another aspect of the invention, an assay is provided in which two or more distinct "label extender" molecules are used; as noted before, label extender molecules are bridging probes which bind to the analyte as well as to label probes, either directly, as in U.S. Pat. No. 4,868,105, or indirectly through amplification multimers, as in U.S. Pat. No. 5,124,246. Multiple label extenders must bind to the analyte in order for a positive signal (indicating presence of the analyte in the sample) to be generated.

In another related aspect of the invention, an assay is provided in which the melt temperature $T_{m1}$ of the multi-component complex formed between the analyte and an amplification multimer or label probe, mediated by two or more distinct label extender molecules, is significantly higher than the melt temperature $T_{m2}$ of each two-component complex formed between an amplification multimer or label probe and an individual label extender molecule. In this aspect, the assay is carried out at conditions which favor formation of hybrid complexes in which analyte molecule is bound to the amplification multimers or label probes. This technique is premised on the enhanced stability of the multi-component complex relative to the much less stable two-component complexes. A preferred method of favoring analyte-amplification multimer hybrid complexes includes running one or more steps of the assay at a temperature between $T_{m1}$ and $T_{m2}$.

In still another aspect of the invention, amplification assays are carried out with two distinct amplification multimers which are bridged by one or more label probes. Each label probe contains two regions, each approximately 5 to 40 nucleotides in length, preferably 10 to 20 nucleotides in length, which are complementary to corresponding regions in each amplification multimer. The length of the complementary regions is selected so as to ensure that the melting temperature of the complex formed between the label probe and a single amplification multimer will be lower, preferably at least about 10° C. lower than the melting temperature of the complex formed between the two amplification multimers, mediated by one or more label probes. Thus, as with the assays described above, an individual multimer will not form a stable hybrid with an individual label probe; however, multi-component hybrid complexes formed from at least one label probe and at least two multimers are stable. Since the multicomponent complex is more likely to form when the amplification multimers are placed in proximity through binding to analyte, this technique produces a more target-dependent signal.

In yet another aspect of the invention, a variation on the aforementioned assay is provided in which two distinct label probes are provided, wherein the two distinct label probes must bind together in order for a signal to be produced. As with the preceding assays, specificity is enhanced as a result of the additional probe sets and the additional hybridization steps which must take place in order for a detectable signal to be generated.

The invention also encompasses variations on the aforementioned assays, in which, for example, oligonucleotide competitors are incorporated into the assay so as to bind to the capture probes (thus reducing the likelihood of nonspecific hybridization on the solid support), and wherein shorter capture probes are used (again, to reduce the likelihood of nonspecific hybridization on the support). Oligonucleotide competitors may also be used to inhibit binding between the label extenders and the amplification multimers, or between the label probes and the amplification multimers.

Further, the invention encompasses methods for compensating for the loss in signal which can result from the various techniques provided herein for reducing background noise. These methods involve the use of preamplifier molecules which serve as intermediate moieties between label extender molecules and amplification multimers, and are structured so as to bind a plurality of amplification multimers. In this way, the number of label probes per label extender can be vastly increased.

The invention additionally encompasses a method for carrying out a hybridization assay in which each of the aforementioned techniques are combined, i.e., in which two or more distinct label extender molecules are used, two or more distinct capture extender molecules are used, amplification multimers and label probes are structured such that label probes bridge adjacent multimers, and the like.

Finally, the invention encompasses kits containing the reagents necessary to carry out the solution phase sandwich hybridization assays described and claimed herein.

BRIEF DESCRIPTION OF THE FIGURES

FIG. 1 diagrams a nucleic acid hybridization assay of the prior art.

FIGS. 8 and 9 show different ways in which two capture extenders bind to a single capture probe.

FIG. 10 is an example of the improved nucleic acid hybridization assay of the present invention using multiple capture extender molecules that bind to the same or different capture probes, one per probe.

DETAILED DESCRIPTION OF THE INVENTION

Definitions and Nomenclature

Figure 2:
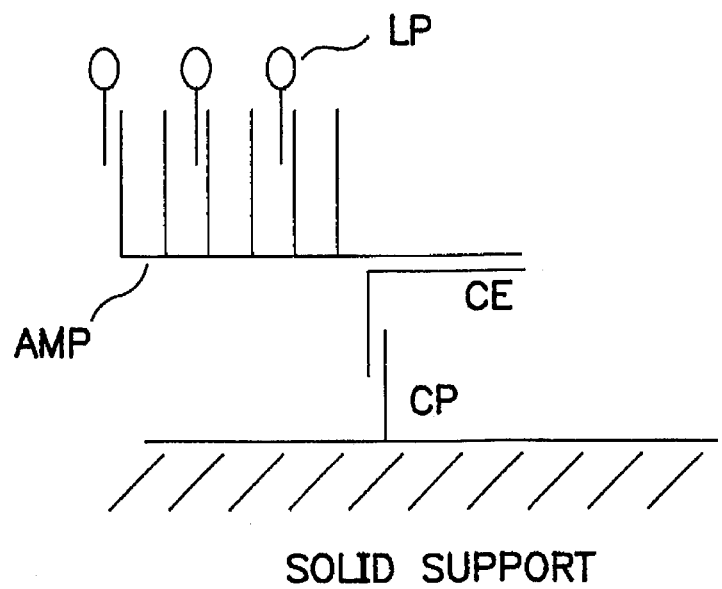
FIGS. 2 through 7 are specific examples of noise-producing hybridization events.

Before the present invention is disclosed and described in detail, it is to be understood that this invention is not limited to specific assay formats, materials or reagents, as such may, of course, vary. It is also to be understood that the terminology used herein is for the purpose of describing particular embodiments only and is not intended to be limiting.

In this specification and in the claims which follow, reference will be made to a number of terms which shall be defined to have the following meanings:

As used herein, the terms "polynucleotide" and "oligonucleotide" shall be generic to polydeoxyribonucleotides (containing 2-deoxy-D-ribose), to polyribonucleotides (containing D-ribose), to any other type of polynucleotide which is an N-glycoside of a purine or pyrimidine base, and to other polymers containing nonnucleotidic backbones (e.g., peptide nucleic acids (PNAs) and synthetic sequence-specific nucleic acid polymers commercially available from the Antivirals, Inc., Corvallis, Oreg., as Neugene™ polymers) or nonstandard linkages, providing that the polymers contain nucleobases in a configuration which allows for base pairing and base stacking, such as is found in DNA and RNA. There is no intended distinction in length between the term "polynucleotide" and "oligonucleotide," and these terms will be used interchangeably. These terms refer only to the primary structure of the molecule. Thus, these terms include double- and single-stranded DNA, as well as double- and single-stranded RNA and DNA:RNA hybrids, and also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.) and with charged linkages (e.g., phosphorothioates, phosphorodithioates, etc.), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides will also include modifications on the sugar moiety, e.g., wherein one or more of the hydroxyl groups are replaced with halogen, aliphatic groups, or are functionalized as ethers, amines, or the like.

The term "polynucleotide analyte" refers to a single- or double-stranded nucleic acid molecule which contains a target nucleotide sequence. The analyte nucleic acids may be from a variety of sources, e.g., biological fluids or solids, food stuffs, environmental materials, etc., and may be prepared for the hybridization analysis by a variety of means, e.g., addition of proteinase K/SDS, chaotropic salts, or the like, or phenol/chloroform extraction. The term "polynucleotide analyte" is used interchangeably herein with the terms "analyte," "analyte nucleic acid," "target" and "target molecule."

As used herein, the term "target region" or "target nucleotide sequence" refers to a probe binding region contained within the target molecule. The term "target sequence" refers to a sequence with which a probe will form a stable hybrid under desired conditions.

As used herein, the term "probe" refers to a structure comprised of a polynucleotide, as defined above, which contains a nucleic acid sequence complementary to a nucleic acid sequence present in the target molecule. The polynucleotide regions of probes may be composed of DNA, and/or RNA, and/or synthetic nucleotide analogs.

It will be appreciated that the binding sequences need not have perfect complementarity to provide stable hybrids. In many situations, stable hybrids will form where fewer than about 10% of the bases are mismatches, ignoring loops of four or more nucleotides. Accordingly, as used herein the term "complementary" intends to refer to an oligonucleotide that forms a stable duplex with its "complement" under assay conditions, generally where there is about 90% or greater homology.

The terms "nucleic acid multimer" or "amplification multimer" are used herein to refer to a linear or branched polymer of the same repeating single-stranded oligonucleotide segment or different single-stranded polynucleotide segments, each of which contains a region where a label probe can bind, i.e., contains a nucleic acid sequence complementary to a nucleic acid sequence contained within a label probe; the oligonucleotide segments may be composed of RNA, DNA, modified nucleotides or combinations thereof. At least one of the segments has a sequence, length, and composition that permits it to bind specifically to a target sequence in a label probe; additionally, at least one of the segments has a sequence, length, and composition that permits it to bind specifically to a target sequence in a label extender or preamplifier. Typically, such segments will contain approximately 15 to 50, preferably 15 to 30, nucleotides, and will have a GC content in the range of about 20% to about 80%. The total number of oligonucleotide segments in the multimer will usually be in the range of about 3 to 1000, more typically in the range of about 10 to 100, and most typically about 50. The oligonucleotide segments of the multimer may be covalently linked directly to each other through phosphodiester bonds or through interposed linking agents such as nucleic acid, amino acid, carbohydrate or polyol bridges, or through other cross-linking agents that are capable of cross-linking nucleic acid or modified nucleic acid strands. Alternatively, the multimer may be comprised of oligonucleotide segments which are not covalently attached, but are bonded in some other manner, e.g., through hybridization. Such a multimer is described, for example, in U.S. Pat. No. 5,175,270 to Nilsen et al. The site(s) of linkage may be at the ends of the segment (in either normal, 3'-5' orientation or randomly oriented) and/or at one or more internal nucleotides in the strand. In linear multimers the individual segments are linked end-to-end to form a linear polymer. In one type of branched multimer three or more oligonucleotide segments emanate from a point of origin to form a branched structure. The point of origin may be another nucleotide segment or a multifunctional molecule to which at least three segments can be covalently bound. In another type, there is an oligonucleotide segment backbone with one or more pendant oligonucleotide segments. These latter-type multimers are "fork-like," "comb-like" or combination "fork-" and "comb-like" in structure, wherein "comb-like" multimers, the preferred multimers herein, are polynucleotides having a linear backbone with a multiplicity of sidechains extending from the backbone. The pendant segments will normally depend from a modified nucleotide or other organic moiety having appropriate functional groups to which oligonucleotides may be conjugated or otherwise attached. The multimer may be totally linear, totally branched, or a combination of linear and branched portions. Typically, there will be at least two branch points in the multimer, more preferably at least three, more preferably in the range of about 5 to 30, although in some embodiments there may be more. The multimer may include one or more segments of double-stranded sequences. Further information concerning multimer synthesis and specific multimer structures may be found in commonly owned U.S. Pat. No. 5,124,246 to Urdea et al.

Commonly assigned U.S. patent application Ser. No. 07/813,588 describes the comb-type branched multimers which are particularly preferred in conjunction with the present method, and which are composed of a linear backbone and pendant sidechains; the backbone includes a segment that provides a specific hybridization site for analyte nucleic acid or nucleic acid bound to the analyte, whereas the pendant sidechains include iterations of a segment that provide specific hybridization sites for a labeled probe.

A first type of preferred comb-type polynucleotide multimer may be represented by the following schematic formula (I):

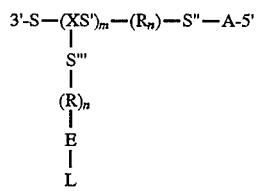

where S is a first spacer segment of at least about 15 nucleotides, preferably about 15 to 50 nucleotides, X is a multifunctional nucleotide that provides a branch site, S' is a branching site spacer segment of 0 to about 15 nucleotides, preferably 0 to 10 nucleotides, m is an integer equal to or greater than 15, preferably in the range of 15 to 100, R is a cleavable linker molecule, n is 0 or 1, S" is a second spacer segment of about 0 to 10 nucleotides, preferably 5 to 10 nucleotides, A is a segment that is capable of hybridizing specifically to analyte nucleic acid or nucleic acid bound to analyte, S'" is a third spacer segment of 0 to 10 nucleotides, E is an oligonucleotide extension of 5 to 10 nucleotides and L is a segment containing 2 to 10 iterations, preferably 3 to 6 iterations, of a nucleotide sequence that is capable of hybridizing specifically to a labeled oligonucleotide probe.

A second type of preferred embodiment of these comb-type polynucleotide multimers may be represented by the following schematic formula (II):

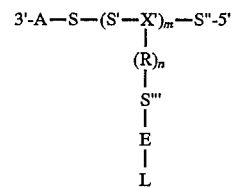

where A is a segment that is capable of hybridizing specifically to analyte nucleic acid or nucleic acid bound to analyte, S is a first spacer segment of at least about 15 molecules, preferably about 15 to 50 molecules, X' is a monomeric molecule that provides a branch site, S' is a branching site spacer segment of 0 to about 15 molecules, preferably 0 to 10 molecules, m is an integer equal to or greater than 15, preferably in the range of 15 to 100, S" is a second spacer segment of about 0 to 10 molecules, preferably 5 to 10 molecules, R is a cleavable linker molecule, n is 0 or 1, S'" is a third spacer segment of 0 to 10 molecules, E is an oligonucleotide extension of 5 to 10 nucleotides and L is a segment containing 2 to 10 iterations, preferably 3 to 6 iterations, of a nucleotide sequence that is capable of hybridizing specifically to a labeled oligonucleotide probe.

The entire backbone of the multimer or the portion thereof from S to S", inclusive, and the portion of the sidechain excluding L will typically be synthesized chemically as an integral unit using conventional automated solid-phase oligonucleotide synthesis chemistry and equipment. In this regard, the spacer segment S serves to space the portion of the molecule that contains the branching sites from the solid phase (the 3' end of S is bound directly or indirectly to the surface of the solid phase). In other embodiments the entire backbone and the pendant sidechains including L may be synthesized as an integral unit.

The modified nucleotides or branching monomer designated X or X' in the above formulae may be a multifunctional nucleotide in which one functional group is used for sidechain extension and the others are used for backbone bonds. Examples of multifunctional nucleotides are described in EPA 883096976 (U.S. Ser. No. 340,031), the disclosure of which is incorporated herein by reference. These modified nucleotides are preferably of the formula:

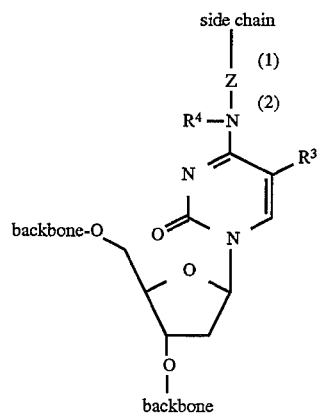

where $R^3$ is hydrogen, methyl, I, Br or F, $R^4$ is hydrogen or methyl, Z is selected from the group consisting of

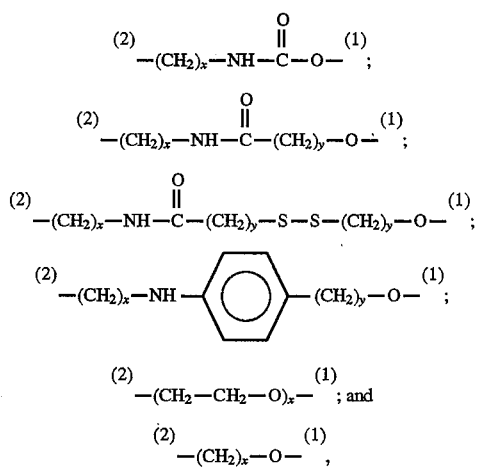

wherein x and y may be the same or different and are integers in the range of 1 to 8, inclusive. (The designations "(1)" and "(2)" at the Z linkage indicate the orientation of the Z linker moiety.)

For multimers of Formula I, as indicated, the spacer segment S' is optional and may be used, if desired, to space each branch site from preceding/succeeding flanking branch sites or a series of adjacent branch sites from flanking series of branch sites. The second spacer segment S" is also optional and may be employed to space the branched portion of the molecule from the segment A to which the analyte is ultimately bound (through one or more intermediate molecules such as label extenders and preamplifiers). Such spacing has been found to improve the binding between the analyte and the multimer. Likewise, the third spacer segment S''' is optional. It is preferably polyT.

For multimers of Formula II, as indicated, the spacer segment S' is optional and may be used, if desired, to space each branch site from preceding/succeeding flanking branch sites or a series of adjacent branch sites from flanking series of branch sites. Likewise, the spacer segment S''' is optional. S, S', S", and S''' may comprise nucleotidic or nonnucleotidic molecules. An example of a nonnucleotidic molecule which may be used in a spacer segment is the clearable linker molecule R, described below.

Segment A has a sequence and length that permits it to bind specifically and stably to a nucleic acid, such as a label extender or a preamplifier, which is bound to the analyte. In order to achieve such specificity and stability segment A will normally be 15 to 50, preferably 15 to 30, nucleotides in length. The specific length and sequence of this segment will, of course, vary depending upon the nucleic acid to which it is intended to hybridize.

Segment E is a sidechain extension that is chemically synthesized using automated solid-phase oligonucleotide synthesis equipment and techniques. It is typically about 5 to 10 nucleotides in length an serves as a site to which segment L may be ligated enzymatically or chemically.

Segment L comprises iterations of an oligomer segment that is capable of hybridizing specifically and stably to a labeled oligonucleotide probe. These segments are also typically 15 to 150, preferably 15 to 120, nucleotides in length. Each L segment will normally contain 2 to 10 iterations of the segment, preferably 3 to 6 iterations. Some sidechains may not include an L segment. Normally at least about 50% of the sidechains, preferably at least about 70% of the sidechains, will include an L segment.

The clearable linker molecules (R) in the backbone and/or sidechains are optional, but preferred. They provide selectable cleavage sites so that samples of the large, comb-type polynucleotide may be cleaved for analysis and characterization purposes. In this regard it is preferred that there be cleavage sites in each sidechain and additional cleavage sites just 5' or the 5'-most branch site (for multimers of formula I) or where the sidechain joins the backbone (for multimers of formula II). Examples of cleavable linker molecules that may be incorporated into the polynucleotides are disclosed in EPA 883096976.

The polynucleotides of the invention may be assembled using a combination of solid phase direct oligonucleotide synthesis, enzymatic ligation methods, and solution phase chemical synthesis as described in detail in U.S. Ser. No. 07/813,588.

As noted above, a "preamplifier" molecule may also be used, which serves as a bridging moiety between the label extender molecules and the amplification multimers. In this way, more amplifier and thus more label is bound in any given target-probe complex. Preamplifier molecules may be either linear or branched, and typically contain in the range of about 30–3000 nucleotides. In the preferred embodiment herein, the preamplifier molecule binds to at least two different label extender molecules, such that the overall accuracy of the assay is increased (i.e., because, again, a plurality of hybridization events are required for the probe-target complex to form).

As used herein, a "biological sample" refers to a sample of tissue or fluid isolated from an individual, including but not limited to, for example, plasma, serum, spinal fluid, semen, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components). Preferred uses of the present method are in detecting and/or quantitating (a) viral nucleic acids, such as from hepatitis B virus ("HBV"), hepatitis C virus ("HCV"), hepatitis D virus ("HDV"), human immunodeficiency virus ("HIV"), and the herpes family of viruses, including herpes zoster (chicken pox), herpes simplex virus I & II, cytomegalovirus, Epstein-Barr virus, and the recently isolated Herpes VI virus, and (b) bacterial nucleic acids, such as Chlamydia, Mycobacterium tuberculosis, etc.

As used herein, the term "nonspecific hybridization" is used to refer to those occurrences in which a segment of a first polynucleotide which is intended to hybridize to a segment of a selected second polynucleotide instead hybridizes to a third polynucleotide, triggering an erroneous result, i.e., giving rise to a situation where label may be detected in the absence of target molecule.

As used herein, the term "nonspecific binding" is used to refer to those occurrences in which a polynucleotide binds to the solid support through an interaction—which may be either direct or indirect—that does not involve hybridization.

Referring now to the preferred embodiment represented in FIG. 1, the following terms apply to the hybridization assay depicted therein.

"Label extender molecules (LEs)," also referred to herein as "label extenders," contain regions of complementarity vis-à-vis the analyte polynucleotide and to the amplifier multimer ("AMP"). If a preamplifier is used (not shown in the figure), the label extender molecules will bind to this intermediate species rather than directly to the amplifier multimer. If neither preamplifier nor amplifier is used, the label extender molecules will bind directly to a sequence in the label probe ("LP"). Thus, label extender molecules are single-stranded polynucleotide chains having a first nucleic acid sequence L-1 complementary to a sequence of the analyte polynucleotide, and a second region having a multimer recognition sequence L-2 complementary to a segment M-1 of label probe, amplifier multimer or preamplifier.

"Label probes (LPs)" are designed to bind either to the label extender, or, if an amplification multimer is employed in the assay, to the repeating oligonucleotide segments of the multimer. LPs either contain a label or are structured so as to bind to a label. Thus, LPs contain a nucleic acid sequence L-3 complementary to a nucleic acid sequence M-2 present within the label probe or the repeating oligonucleotide segments of the multimer and are bound to, or structured so as to bind to, a label which provides, directly or indirectly, a detectable signal.

"Capture extender molecules (CEs)," also referred to herein as "capture extenders," bind to the analyte polynucleotide and to capture probes, which are in turn bound to a solid support. Thus, capture extender molecules are single-stranded polynucleotide chains having a first polynucleotide sequence region containing a nucleic acid sequence C-1 which is complementary to a sequence of the analyte, and a second, noncomplementary region having a capture probe recognition sequence C-2. The sequences. C-1 and L-1 are nonidentical, noncomplementary sequences that are each complementary to physically distinct sequences of the analyte.

"Capture probes (CPs)" bind to the capture extenders and to a solid support. Thus, as illustrated in FIG. 1, capture probes have a nucleic acid sequence C-3 complementary to the C-2 sequence of a CE and are covalently (or otherwise tightly) bound to a solid support.

Generally, solution phase hybridization assays carried out using the system illustrated in FIG. 1 proceed as follows. Single-stranded analyte nucleic acid is incubated under hybridization conditions with the capture extenders and label extenders. The resulting product is a nucleic acid complex of the analyte polynucleotide bound to the capture extenders and to the label extenders. This complex may be subsequently added under hybridizing conditions to a solid phase having the capture probes bound to the surface thereof; however, in a preferred embodiment of this invention, the initial incubation is carried out in the presence of the support-bound capture probes. The resulting product comprises the complex bound to the solid phase via the capture extender molecules and capture probes. The solid phase with bound complex is then optionally separated from unbound materials. An amplification multimer, preferably a comb-type multimer as described above, is then optionally added to the solid phase-analyte-probe complex under hybridization conditions to permit the multimer to hybridize to the LEs; if preamplifier probes are used, the solid phase-analyte-probe complex is incubated with the preamplifier probes either along with the amplification multimer or prior to incubation with the amplification multimer. The resulting solid phase complex is then separated from any unbound preamplifier and/or multimer by washing. The label probes are then added under conditions which permit hybridization to the LEs, or, if an amplification multimer was used, to the repeating oligonucleotide segments of the multimer. The resulting solid phase labeled nucleic acid complex is then washed to remove unbound labeled oligonucleotide, and remaining label is measured. It should be noted that the components represented in FIG. 1 are not necessarily drawn to scale, and that the amplification multimers, if used, contain a far greater number of repeating oligonucleotide segments than shown (as explained above), each of which is designed to bind a label probe.

Figure 3:
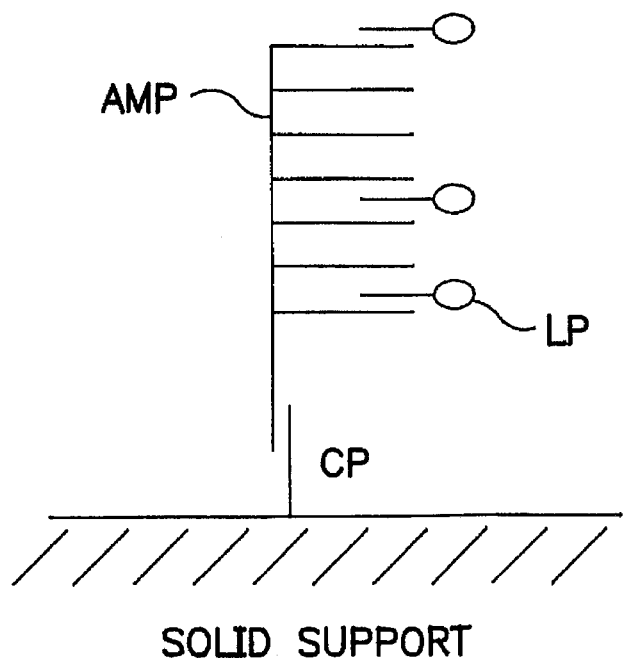
Figure 4:
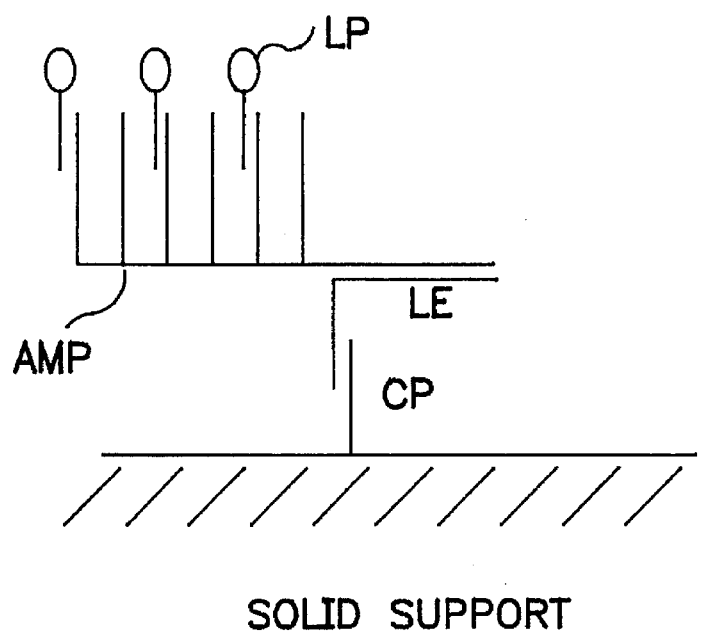
Figure 5:
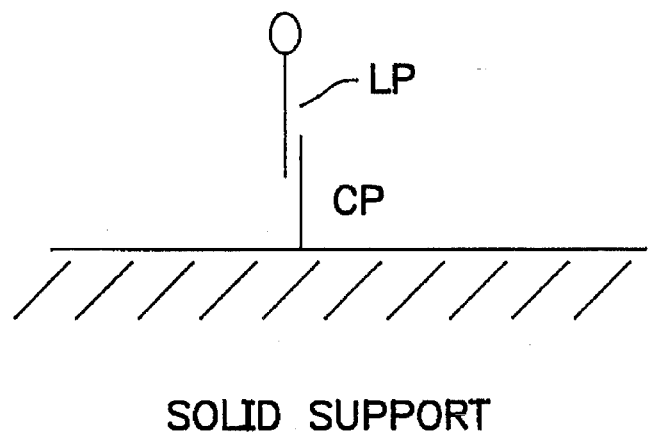
Figure 6:
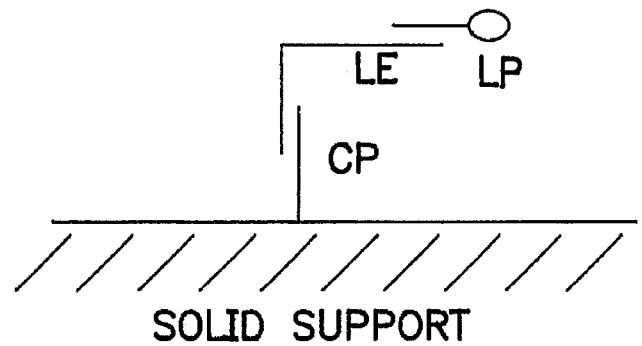
Figure 7:
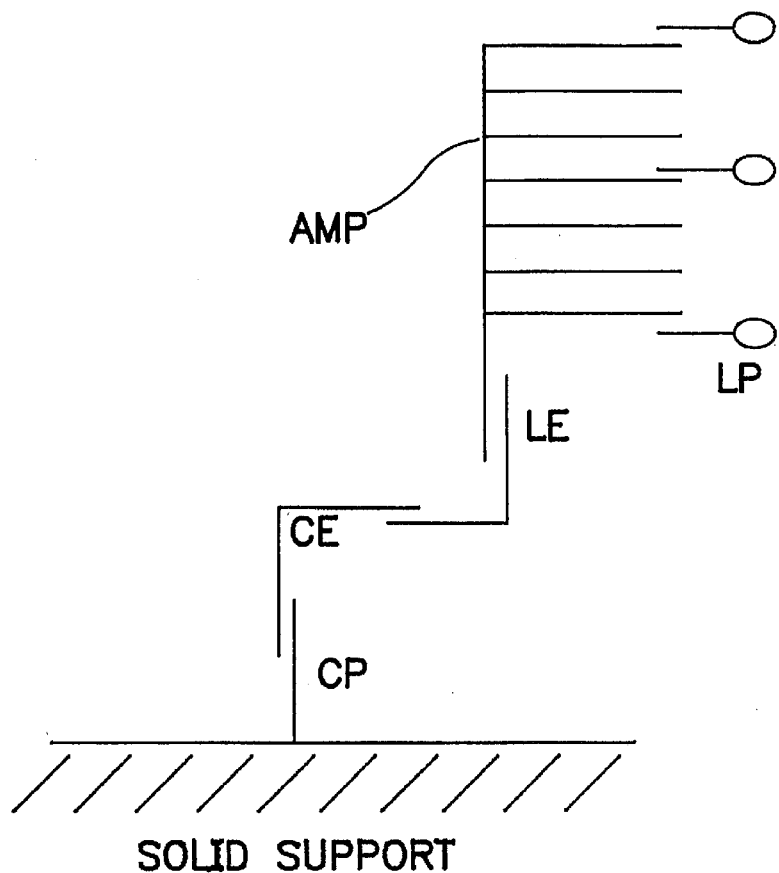

As will be appreciated by those skilled in the art, the techniques of the present invention may be used in conjunction with a wide variety of assay formats. However, for simplicity, the present techniques will be discussed in terms of the aforementioned solution phase hybridization assay using amplification multimers, which represents the preferred embodiment herein. Various sources of background noise which can arise in such an assay are illustrated in FIGS. 2 through 7. It will be noted that each of these figures depicts a situation where label will be detected on the solid support in the absence of target. In FIGS. 3, 4 and 5, nucleotide sequences present in the amplifier molecule, the label extender and the label probe, respectively, bind to the capture probe rather than to the desired sequences. In FIGS. 2, 6 and 7, the capture probe has hybridized to the capture extender molecule properly, but an incorrect molecule has then hybridized to the capture extender. In FIG. 2, the amplifier has hybridized directly to the capture extender, in the absence of target molecule, while in FIGS. 6 and 7, the label probe and the label extender have hybridized directly to the capture extender, again giving rise to a situation where label will be detected in the absence of analyte. It will be appreciated, however, that other such erroneous—i.e., "nonspecific"—hybridization and binding scenarios can be envisioned wherein a signal is generated in the absence of target. The techniques of the invention address these other potential sources of background noise as well.

The primary focus of the present method is on eliminating a number of sources of background noise, by maximizing the interaction of capture extender and label extender probes with the target molecule, minimizing the interaction of capture probes and capture extender molecules with the label probes, label extender molecules and amplifiers, increasing the number of probes and/or hybridization steps necessary to give rise to a target-dependent signal, and reducing the likelihood that incorrect moieties will bind to the support-bound capture probes.

In a first embodiment of the invention, a hybridization assay is provided which is configured such that the temperature $T_{m1}$ at which the target molecule "melts" from the support-bound capture probes (defined as the temperature at which 50% of the individual capture probes participating in target molecule/capture extender/capture probe complexes are no longer bound to the target molecule) is significantly higher than the temperature $T_{m2}$ at which an individual capture extender molecule "melts" from a single capture probe. This procedure may be used in virtually any type of hybridization assay wherein capture probes and capture extender molecules are used, including a wide range of solution phase hybridization assays, amplification assays, filter hybridization methods, assays involving the polymerase chain reaction ("PCR"), and the like. One example of a hybridization assay with which the present technique is useful is that described in U.S. Pat. No. 4,868,105 to Urdea et al., or, preferably, that described above in conjunction with the configuration illustrated in FIG. 1 and described above. This method is premised on the design and construction of hybrid complexes such that the melt temperature $T_{m1}$ at which the analyte dissociates from the capture probe in the capture probe-capture extender-analyte hybrid is at least about 5° C. greater than, preferably at least about 10° C. greater than the melt temperature $T_{m2}$ at which a capture extender dissociates from a capture probe in the capture probe-capture extender hybrid.

This stability difference is exploited in the assay by conducting at least one step in the assay under stringency conditions which favor the $T_{m1}$ complex formation, but disfavor the $T_{m2}$ complex formation. Stringency can be controlled by altering a step parameter which is a thermodynamic variable. Such variables are well known in the art, and include formamide concentration, salt concentration, chaotropic salt concentration, pH (hydrogen ion concentration), organic solvent content, and temperature. "Chaotropic salt" refers to a salt that acts as a hydrophobic bond breaker, including the trihaloacetates, isothiocyanate and perchlorate. Hamaguchi et al., *J. Am. Chem. Soc.* (1962) 84:1329–1338. A preferred stringency control is temperature: at least one assay step is conducted at a temperature between $T_{m1}$ and $T_{m2}$, more preferably about midway between the two temperatures. A preferred step at which stringency is exercised is the initial hybridization step in the assay, in which target is incubated with capture extender molecules and support bound capture probes. Thus, in a preferred embodiment, the initial hybridization step is carried out at a temperature which is higher than $T_{m2}$ but lower than $T_{m1}$. Since nonspecifically hybridized molecules can bind through the capture probe and capture extender molecules (as illustrated in FIGS. 2, 6 and 7), this method significantly reduces certain types of nonspecific hybridization.

It will be readily apparent to one skilled in the art that the greater the temperature difference between $T_{m1}$ and $T_{m2}$, the greater the "efficiency" of this technique in removing background noise. Thus, one skilled in the art will recognize that temperature differentials of less than 10° C., even less than 5° C., would also permit reduction of background noise, albeit to a lesser extent. One could increase efficiency in such situations by increasing the number of steps which utilize appropriate stringency conditions, or by repeating a single stringent step.

Preferably, the method is carried out using at least two distinct capture extender molecules, each of which binds to a distinct segment of the analyte. The capture extender molecules comprise a first nucleotide sequence complementary to a segment of analyte and a second nucleotide sequence complementary to a capture probe. This assay has two primary topological embodiments.

Figure 8:
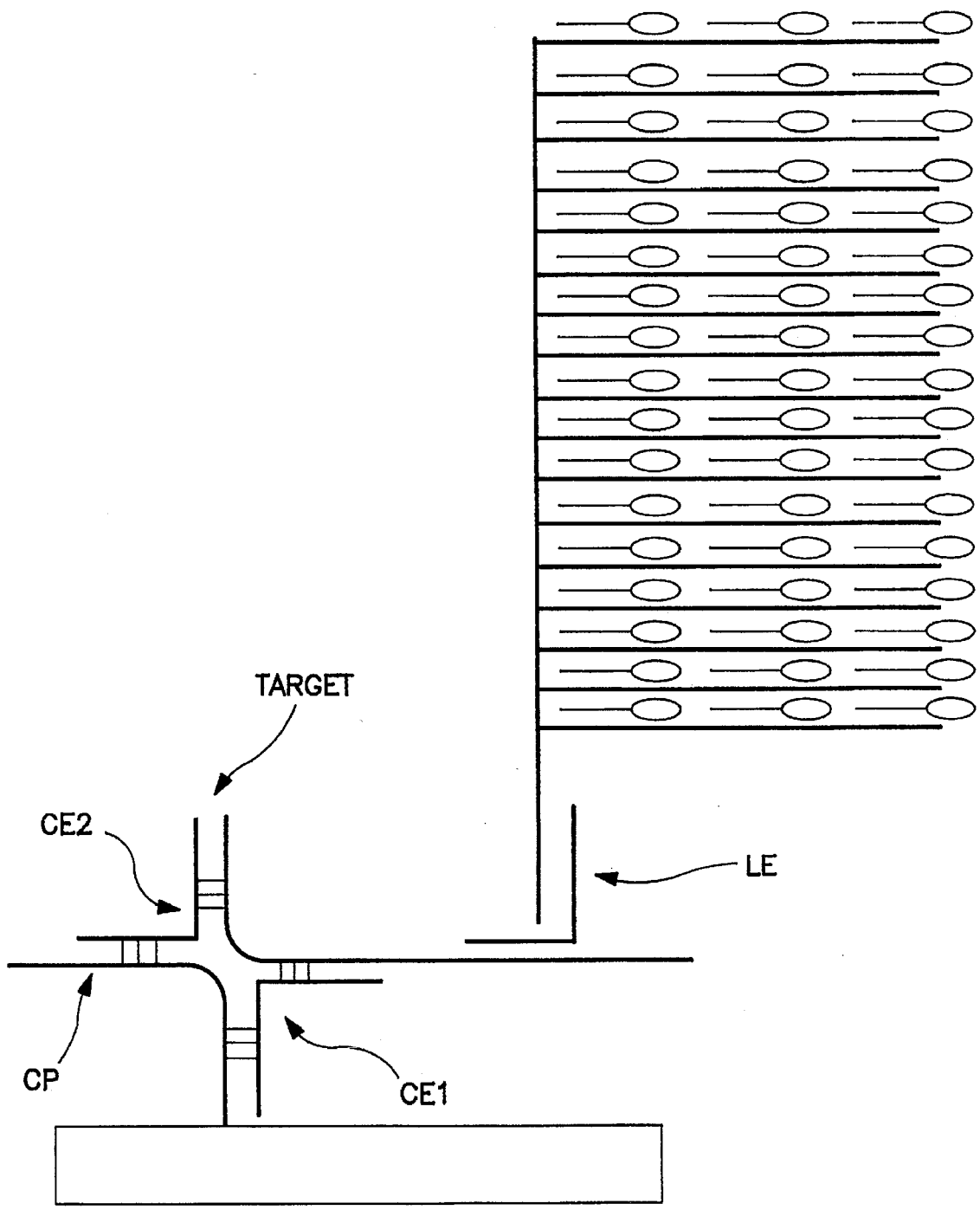
FIGS. 8, 9 and 10 are examples of the improved nucleic acid hybridization assay of the present invention in which capture extender molecules are required to bind a target to the solid support.
Figure 9:
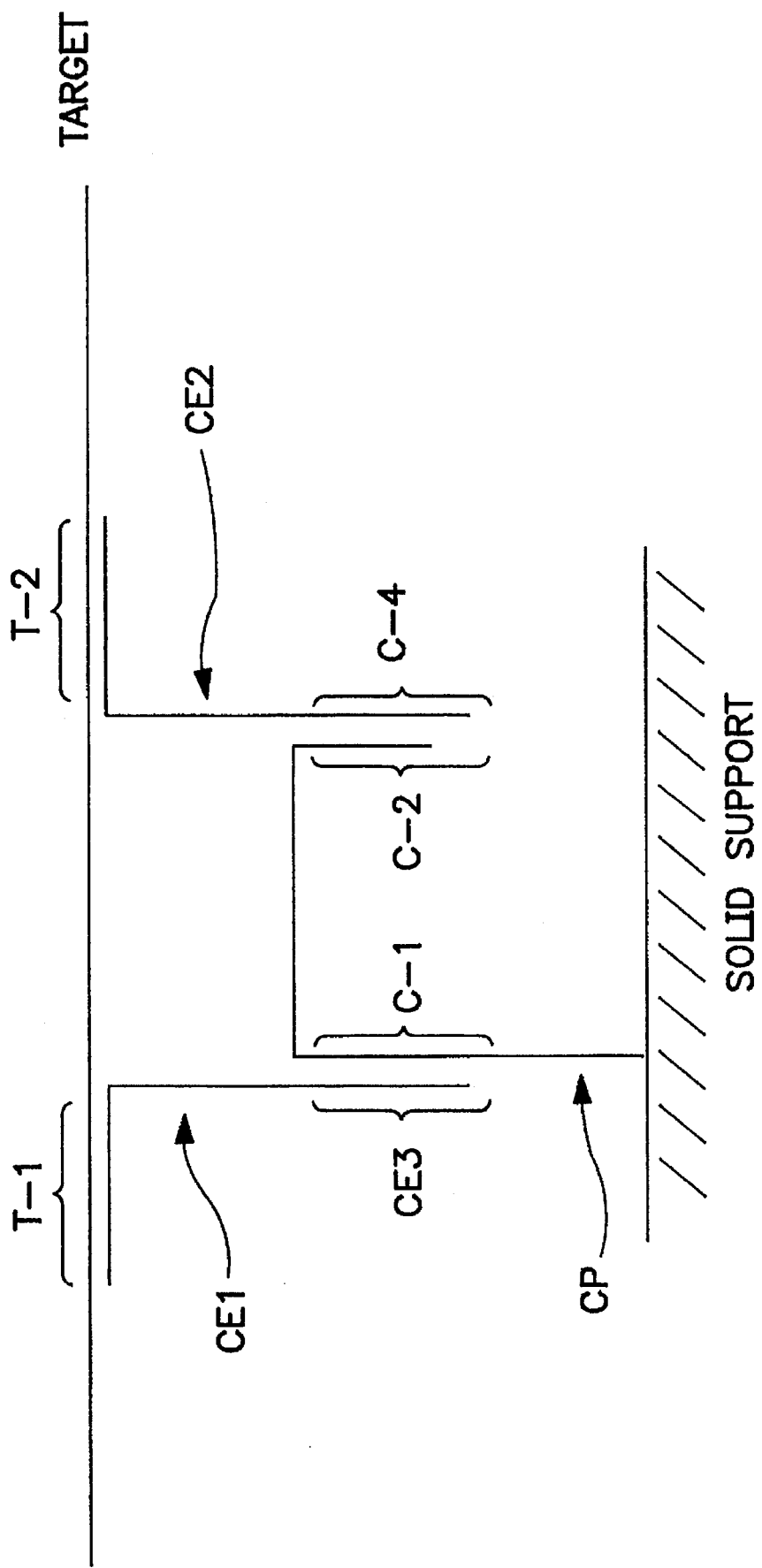

A first embodiment of this assay configuration in which two distinct capture extender molecule are used is illustrated in FIGS. 8 and 9. In this embodiment, the two distinct capture extenders have distinct first nucleotide sequences complementary to distinct but proximate segments of analyte, and also have distinct second nucleotide sequences complementary to distinct segments of a single capture probe. "CE1" and "CE2" represent the two different capture extender molecules, positioned in a cruciform-like structure, such that each extender molecule hybridizes to proximate but distinct segments of target, and to proximate but distinct segments of a single capture probe.

As illustrated in FIG. 9, the capture probe is structured so as to contain: (1) a first nucleotide sequence C-1 which binds to a nucleotide sequence C-3 in first capture extender CE1; and (2) a different nucleotide sequence C-2 which binds to a nucleotide sequence C-4 in second capture extender CE2. CE1 and CE2 then hybridize to distinct, nonoverlapping segments of the analyte molecule. Preferably, sequences C-1, C-2, C-3 and C-4 are relatively short, i.e., less than about 30 nucleotides in length, and preferably in the range of about 10 to 15 nucleotides in length. C-1 and C-2 can be directly adjacent, or separated by a spacer region. In addition, it is preferred that the binding of capture probe to capture extender molecules (i.e., C-1:C-3 and C-2:C-4) be relatively weak ($T_m$ less than about 55°), while the binding of the capture probes to the target through the capture extender molecules be much stronger ($T_m$ greater than about 65°). This allows the target molecule to bind to the solid support with far greater stability, on the order of 100- to 1000-fold, than the capture extender molecules. This method also enables use of fewer capture probes, which in turn reduces the likelihood of nonspecific hybridization as illustrated in FIGS. 3, 4 and 5. This assay is exemplified in the experimental section herein, in Examples 1 and 2.

It will be appreciated by those skilled in the art that the cruciform-type configuration shown in FIG. 8 is for purposes of exemplification only, and that alternative assay configurations employing two or more capture extender molecules are also possible. The only requirement is that the assay be structured such that the target binds to the solid support with a melt temperature greater than that of the capture extenders binding to the capture probe. It will also be appreciated by those skilled in the art that the embodiment of FIG. 9 works equally well if C-1 and C-2 are identical capture probe sequences complementary to identical sequences C-3 and C-4 in the two capture extenders: in this instance, the capture probe contains two copies of the repeat sequence C-1.

Figure 10:
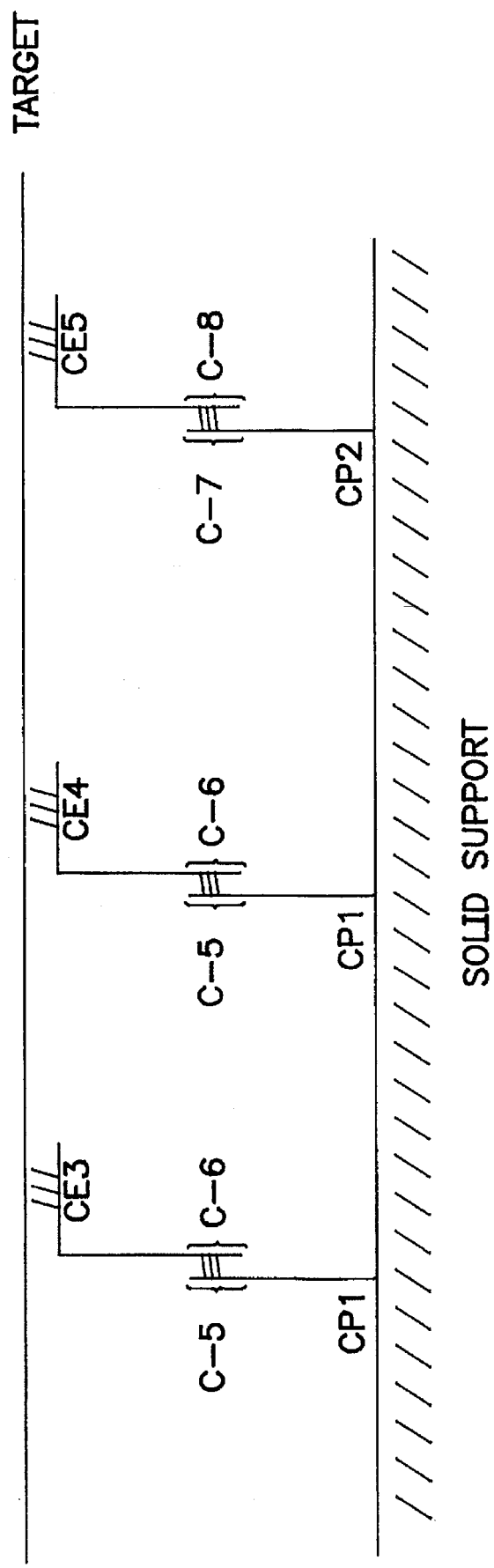

A second embodiment of this assay configuration in which two distinct capture extender molecule are used is illustrated in FIG. 10. In this embodiment, two or more (preferably more than three) distinct capture extenders have distinct first nucleotide sequences complementary to distinct but proximate segments of analyte, and also have second nucleotide sequences complementary to a segment of a capture probe. In this embodiment, only one capture extender binds per capture probe. If all the capture probes in the assay contain a single sequence that binds to the capture extenders, then the capture extenders will all have the same second nucleotide sequence complementary to the binding segment of the capture probe. Alternatively, the assay may use distinct capture probes containing multiple sequences that bind to the capture extenders, in which case the capture extenders will have distinct second nucleotide sequences.

Thus, in FIG. 10, "CE3", "CE4" and "CE5" represent three different capture extenders, such that each capture extender contains distinct first nucleotide sequences that hybridize to distinct segments of target. CE3 and CE4 contain a second nucleotide sequence C-6 which binds to a nucleotide sequence C-5 in a first capture probe CP1; while CE5 contains a different second nucleotide sequence C-8 which binds to a nucleotide sequence C-7 in second capture probe CP2. It will be easily seen that any combination of two or more such capture extenders can be used in this assay.

Another variation on this technique involves the use of two or more distinct label extender molecules, each of which must bind to the target in order for the amplifier probe to bind. This assay is carried out basically as described above with respect to FIG. 1; however, as noted, at least two distinct label extender molecules are incorporated into the assay. The label extenders comprise a first nucleotide sequence complementary to a segment of analyte and a second nucleotide sequence complementary to an amplification multimer (or preamplifier, as discussed below).

Figure 11:
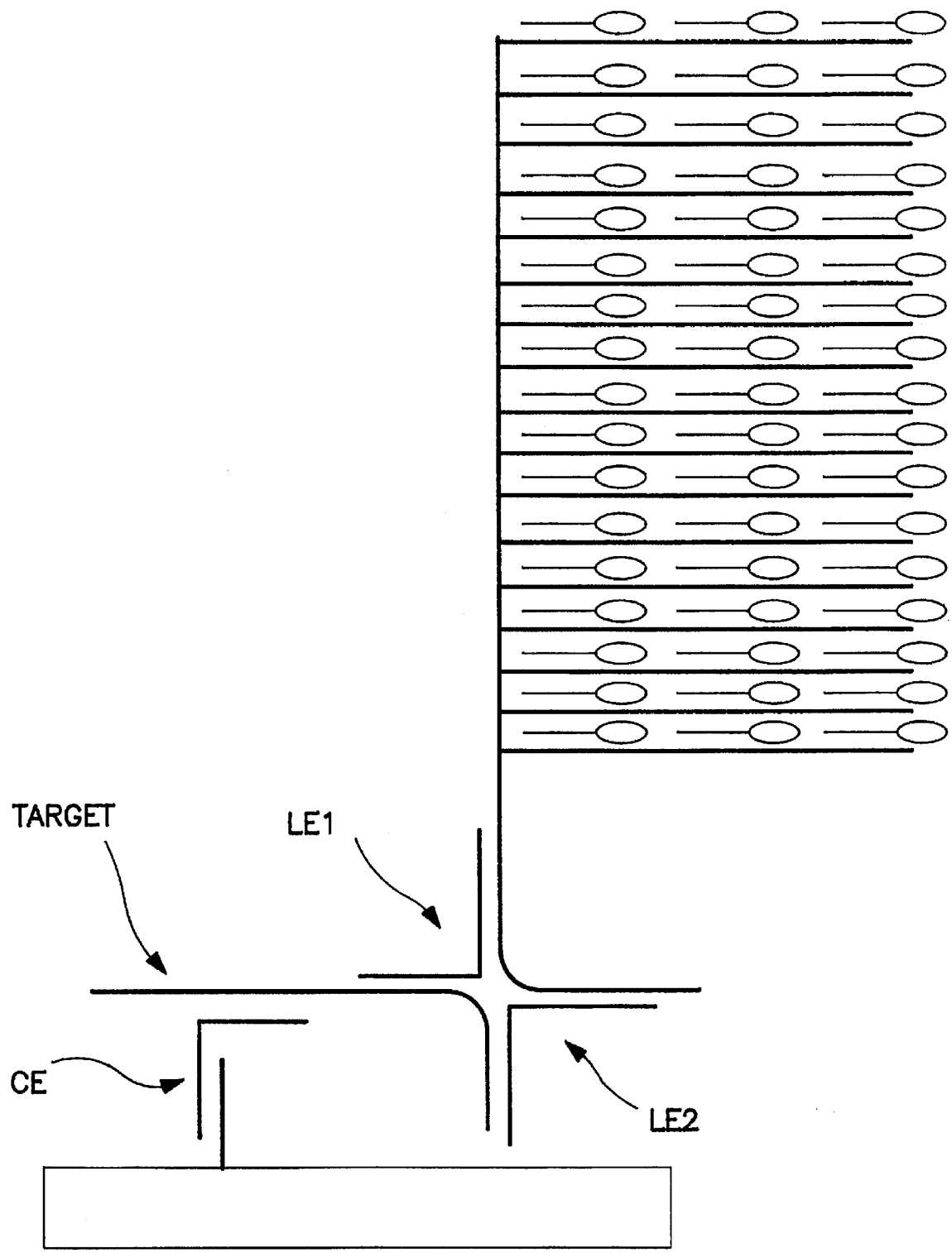
FIG. 11 is an example of the improved nucleic acid hybridization assay of the present invention using label extender molecules that form a cruciform structure.

In this assay configuration in which two distinct label extenders are used is illustrated in FIG. 11. In this embodiment, the two distinct label extenders have distinct first nucleotide sequences complementary to distinct but proximate segments of analyte, and also have distinct second nucleotide sequences complementary to distinct segments of a single amplification multimer. "LE1" and "LE2" represent the two different label extenders positioned in a cruciform-like structure, such that each extender molecule hybridizes to proximate but distinct segments of target, and to proximate but distinct segments of a single amplification multimer. This assay is exemplified in the experimental section herein, in Example 2.

As illustrated in FIG. 11, the amplification multimer is structured so as to contain: (1) a first nucleotide sequence C-1 which binds to a nucleotide sequence C-3 in first label extender LE1; and (2) a different nucleotide sequence C-2 which binds to a nucleotide sequence C-4 in second label extender LE2. LE1 and LE2 then hybridize to distinct, nonoverlapping segments of the analyte molecule. Preferably, sequences C-1, C-2, C-3 and C-4 are relatively short, i.e., less than about 30 nucleotides in length, and preferably in the range of about 10 to 15 nucleotides in length. C-1 and C-2 can be directly adjacent, or separated by a spacer region. In addition, it is preferred that the binding of amplification multimer to label extender molecules (i.e., C-1:C-3 and C-2:C-4) be relatively weak ($T_m$ less than about 45°), while the binding of the amplification multimer to the target through the label extender molecules be much stronger ($T_m$ greater than about 65°). This allows the target molecule to bind to the amplification multimer with far greater stability, on the order of 100- to 1000-fold, than the label extender molecules. Again, as with the preceding method in which at least two capture extender molecules are used, assay specificity is increased by virtue of the additional hybridization steps which are necessary to give rise to a target-dependent signal.

It will be appreciated by those skilled in the art that the cruciform-type configurations shown in FIG. 11 is for purposes of exemplification only, and that alternative assay configurations employing two or more label extender molecules are also possible. The only requirement is that the assay be structured such that the target binds to the amplification multimer with a melt temperature greater than that of the label extenders binding to the amplification multimer. It will also be appreciated by those skilled in the art that this embodiment works equally well if C-1 and C-2 are identical amplification multimer sequences complementary to identical sequences C-3 and C-4 in the two label extenders: in this instance, the amplification multimer contains two copies of the repeat sequence C-1. It will further be appreciated that the preceeding description could be utilized with a preamplifier (as discussed below), wherein the label extenders interact in cruciform structure with the preamplifier rather than directly with the amplification multimer.

Figure 12:
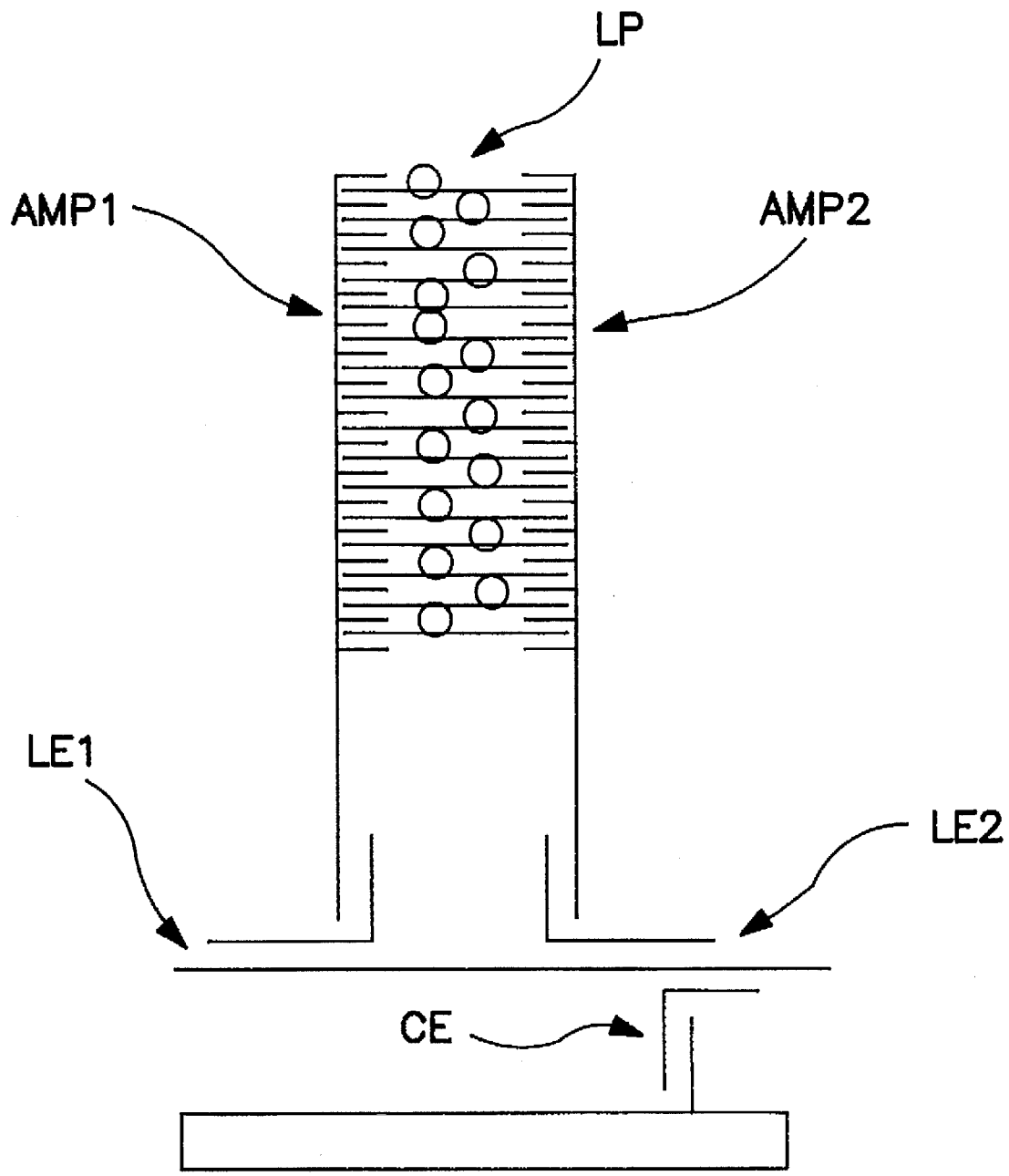
FIG. 12 is an example of the improved nucleic acid hybridization assay of the present invention using multiple amplification multimers and bridging label probes.

In another embodiment of the invention, the phenomenon of target-independent signal generation is addressed by bridging adjacent amplifier molecules in such a way as to reduce virtually all of the principal sources of assay background, including nonspecific hybridization of label extender molecules to capture probes and capture extender molecules, nonspecific hybridization of amplification multimers to capture probes and capture extender molecules and amplifier nonspecific binding. In this embodiment, two distinct amplifier multimers are used, designated AMP1 and AMP2 in FIG. 12, as well as two distinct label extender molecules, designated LE1 and LE2. Neither AMP1 nor AMP2 will retain label unless they are within bridging distance of each other, so that there is a much higher likelihood that the amplifiers are actually bound to the target molecule before labelling occurs. This is accomplished by providing label probes which contain: (1) a first nucleic acid sequence L-1 which contains a nucleic acid sequence complementary to a region in the repeating oligonucleotide subunits of AMP1; (2) a second nucleic acid sequence L-2 which contains a nucleic acid sequence complementary to a region in the repeating oligonucleotide subunits of AMP2; and (3) a detectable label therebetween. L-1, L-2, and the corresponding complementary sequences in the amplifier probes are selected such that the melting temperature of the complex formed from both amplifier probes and the label probes is preferably at least about 10° C. higher than the melting temperature of the complex formed between the label probe and a single amplifier multimer. It will also be appreciated that such a configuration gives rise to the advantages discussed above with respect to the use of multiple probes and consequent additional hybridization steps required to produce a detectable signal.

Figure 13:
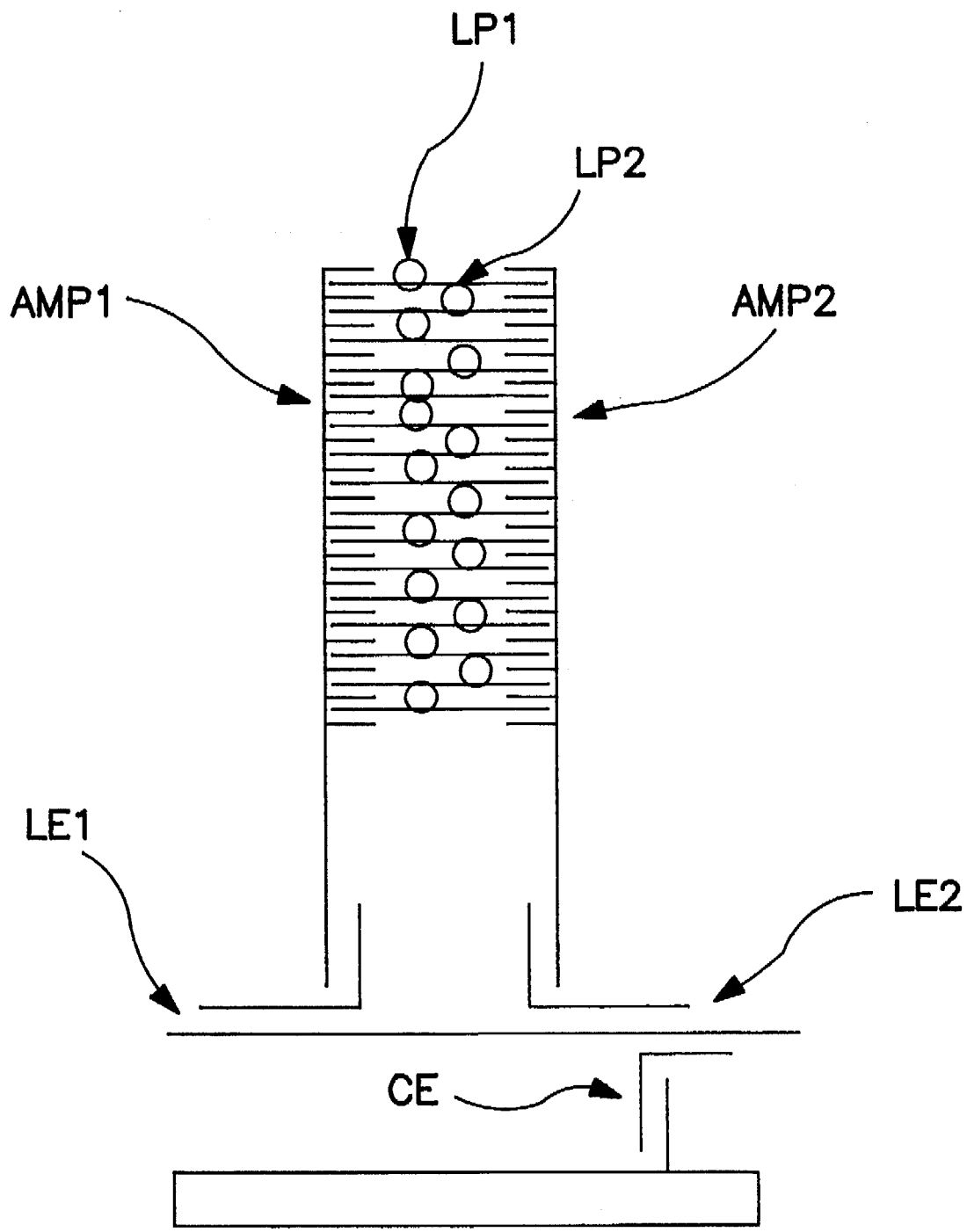
FIG. 13 is an example of the improved nucleic acid hybridization assay of the present invention using multiple amplification multimers and multiple bridging label probes.

In a variation on this embodiment, two or more distinct label probes may be used, either containing two different types of labels, as shown in FIG. 13, or containing an inactive segment of a label which is then activated upon conjugation with a label probe on an adjacent amplifier molecule. Examples of this multi-amplifier, multi-label probe embodiment include those wherein adjacent label probes contain: (a) individual subunits, members or portions of an enzyme such as β-galactosidase; (b) an enzyme and a corresponding co-enzyme (such as a flavoenzyme and FADH or an NAD-linked dehydrogenase and NADH); or (c) enzymes that form a part of a channelling system or cascade system wherein the product of one enzyme is the substrate for the second enzyme (such as the fatty-acid synthetase system). In each case the two label probes contain distinct moieties which do not produce the detectable product unless brought together by the presence of the target and thus amplifier bridging.

In a variation on all of the above embodiments, preamplifier molecules may be used in all of the above embodiments to increase signal. Preamplifiers are added to the assay reaction either concurrently with or prior to the addition of the amplification multimers.

As alluded to earlier, a primary cause of background noise, i.e., signals which are produced and detected independent of target molecule, results from the support-bound capture probes and the fact that polynucleotides other than capture extender molecules can bind thereto. Additional embodiments of the invention derive from this realization. First, solid supports used in hybridization assays like those described above are configured such that the capture probes are shorter, typically less than about 20 nt, and more typically about 15 nt. Second, oligonucleotides containing sequences which are identical to C-2 as illustrated in FIG. 1 are introduced into the assay; such oligonucleotides function as competitors for the capture probes and thus reduce the number of available capture probe hybridization sites (C-3 in FIG. 1). This is illustrated in Example 1.

Experimental

The practice of the present invention will employ, unless otherwise indicated, conventional techniques of synthetic organic chemistry, biochemistry, molecular biology, and the like, which are within the skill of the art. Such techniques are explained fully in the literature. See, e.g., Sambrook, Fritsch & Maniatis, *Molecular Cloning: A Laboratory Manual*, Second Edition (1989); *Oligonucleotide Synthesis* (M. J. Gait, ed., 1984); *Nucleic Acid Hybridization* (B. D. Hames & S. J. Higgins, eds., 1984); and a series, *Methods in Enzymology* (Academic Press, Inc.). All patents, patent applications, and publications mentioned herein, both supra and infra, are hereby incorporated by reference.

It is to be understood that while the invention has been described in conjunction with the preferred specific embodiments thereof, that the description above as well as the examples which follow are intended to illustrate and not limit the scope of the invention. Other aspects, advantages and modifications within the scope of the invention will be apparent to those skilled in the art to which the invention pertains.

In the following examples, efforts have been made to insure accuracy with respect to numbers used (e.g., amounts, temperature, etc.) but some experimental error and deviation should be accounted for. Unless indicated otherwise, temperature is in degrees C and pressure is at or near atmospheric.

Example 1

Amplification Assay Using Different Capture Extenders in a "Cruciform" Format

This example describes a hybridization assay using two or more distinct capture extenders, as illustrated in FIG. 8. The goal of this experimental work was to reduce background signals caused by capture extender probe binding to the solid support. By reducing the ability of capture extender probes to bind to the support, the target polynucleotide is forced to bind through multiple capture extender probes in order to be bound stably to the solid surface, giving rise to an assay background which is as low as in an assay run with no capture extender probes (i.e., because essentially no capture extender molecules would be bound to the support). The experimental work summarized in this example also demonstrates that when molecules capable of competitively binding to the immobilized capture probe are added, it is possible to reduce the background even further, because the likelihood that the label extender molecules or label probes will bind to the support via the immobilized capture probe is significantly reduced.

A capture probe designated CP2 was attached to the solid support. Two pairs of HCV capture extender molecules were designed. The first member of each pair had a 5' sequence complementary to the last 16 nts of capture probe CP2 and the second member of each pair had a 3' sequence complementary to the first 13 nts of CP2. The extenders could thus bind to the solid support as illustrated in FIG. 8. They can bridge neighboring CP2 molecules (as the target in FIG. 10, which has been captured via CEs 3, 4 and 5 to two different CP molecules) or they can form a cruciform with a single CP2 (as the target in FIG. 9, which has bound via CEs 1 and 2 to the same CP molecule). Since the probes are designed optimally to form the cruciform and since the capture probe concentration is kept low, the cruciform should be greatly favored kinetically over the bridging of two neighboring CP2 molecules and the cruciform is presumed to predominate in the equilibrium distribution.

A signal amplification solution phase nucleic acid sandwich hybridization assay format was employed in this example. The signal amplification is generated through a branched DNA multimer (amplifier) which has a first segment (E') that hybridizes to a segment of the label extender probes and up to fifteen iterations of a segment (F), wherein segment F hybridizes to three labeled oligonucleotides. The target nucleic acid is bound to the solid support via an immobilized capture probe and a capture extender probe which hybridizes to both the capture probe and the target. The amplifier multimer is bound to the immobilized target via a label extender probe which hybridizes to both the target and the amplifier multimer. Two competitor probes were also used for background reduction. These probes bind to the capture probe.

The capture extender probes, label extender probes and competitor probes as used in this assay were as follows.

Sequence (5'→3') Capture extender probes (the segment which binds to the immobilized capture probe is underlined):

```
1:
TTTCAGCAATCAGGTGTTCTCGTCCTGGCAATTCCGGTGTACTCACCGGTTC SEQ ID NO: 1
2:
TTTCAGCAATCAGGTGTTCTCWTTCCGGCGATTCCGGTGTACTCACCGGTTC SEQ ID NO: 2
3:
GTATTGAGCGGGTTKMTCCAAGAAAGGACCCGGTCGGCTCTGGGAC SEQ ID NO: 3
4:
GCATAGAGTGGGTTWATCCAAGAAAGGACCCAGTCGGCTCTGGGAC SEQ ID NO: 4
5:
TTTCAGCAATCAGGTGTTCAGCAGTCTTGCGGGGGCACGCCCAAATCTCCAG SEQ ID NO: 5
6:
TTTCAGCAATCAGGTGTTCAGTGATCTTGCGGGGGCGTGCCCAAATCTCCAG SEQ ID NO: 6
7:
TTTCAGCAATCAGGTGTTCAGCAGTCTCGCGGGGGCACGCCCAAATCTCCAG SEQ ID NO: 7
8:
TTTCAGCAATCAGGTGTTCAGCAGTCTTGCGGGGGCACGCCCAAATGGCTGG SEQ ID NO: 8
9:
TTTCAGCAATCAGGTGTTCAGTGATCTCGCGGGGGCACGCCCAAATTTCTGG SEQ ID NO: 9
10:
ACAAGGCCTTTCGCGACCCAACACTACTCGGCT+e,uns TCGGCTCTGGGAC SEQ ID NO: 10
11:
ACAAGGCCKTTCGCAACCCAACGCTACTMGGCTTCGGCTCTGGGAC SEQ ID NO: 11
```

Label extender probes used (the sequence which hybridizes to the amplifier multimer is underlined):

12:
AGGCATAGGACCCGTGTCTTTCCTCACAGGGGAGTGATTCATGGTGGAGTGTC SEQ ID NO: 12
13:
AGGCATAGGACCCGTGTCTTATGGCTAGGCGCTTTCTGCGTGAAGACAGTAGT SEQ ID NO: 13
14:
AGGCATAGGACCCGTGTCTTKCCTGGAGGCTGTACGASACTSGTACTAGCGCC SEQ ID NO: 14
15:
AGGCATAGGACCCGTGTCTTCGCAGACCACTATGGCTCTCCCGGGAGGGGGGG SEQ ID NO: 15
16:
AGGCATAGGACCCGTGTCTTGGGGCACTCGCAAGCACCCTATCAGGCAGTACC SEQ ID NO: 16
17:
AGGCATAGGACCCGTGTCTTTGTGCTCATGKTGCACGGTCTACGAGACCTCCC SEQ ID NO: 17
Competitor probes (these sequences hybridize to the immobilized capture probe):
18:
TCGGCTCTGGGAC SEQ ID NO: 18
19:
CAGCAATCAGGTGTTC SEQ ID NO: 19

The plates used for the assay were coated as follows: White Microlite 1 removawell strips (polystyrene microtiter plates, 96 wells/plate) were purchased from Dynatech Inc.

Each well was filled with 250 μl 1N HCl and incubated at room temperature for 15–20 min. The plates were then washed 1 times with 1×PBS and the wells aspirated to remove liquid. The wells were then filled with 250 μl 1N NaOH and incubated at room temperature for 15–20 min. The plates were again washed 3 times with 1×PBS and the wells aspirated to remove liquid.

Poly(phe-lys) was purchased from Sigma Chemicals, Inc. This polypeptide has a 1:1 molar ratio of phe:lys and an average m.w. of 47,900 gm/mole. It has an average length of 309 amino acids and contains 155 amines/molecule. The polypeptide was mixed with 2M NaCl/1×PBS to a final concentration of 0.1 mg/mL (pH 6.0). 200 μl of this solution was added to each well. The plate was wrapped in plastic to prevent drying and incubated at 30° C. overnight. The plate was then washed 3 times with 1×PBS and the wells aspirated to remove liquid.

To 250 $OD_{260}$ units/ml of the following oligonucleotide:

Capture Probe CP2: 5'-XGTCCCAGAGCCGAGAACACCTGAT-TGCTG-3'  SEQ ID NO:20

(X is the long chain amine modified nucleotide ($N^4$-(6-aminocaproyl-2-aminoethyl) derivative of 5-methylcytidine)) in 50 mM sodium phosphate pH 7.8 was added 180 mg of bis(sulfosuccinimidyl) suberate ($BS^3$). The mixture was vortexed and incubated at room temperature for 30 min. A gel filtration column (Pharmacia Sephadex G-25, NAP-25) equilibrated with 10 mM sodium phosphate pH 6.5 was used to purify the activated oligonucleotide. The activated oligonucleotide reaction mixture was applied to the column and allowed to filter. The eluate was collected and saved for use in the next step. The concentration of the eluate was adjusted to $3.7 \times 10^{-2}$ $OD_{260}$ units/ml using 50 mM sodium phosphate pH 7.8 for dilution.

100 μl of the activated oligonucleotide-containing eluent was added to each well and the wells were incubated at 4° C. for 12–18 hours. The plate was then washed 2 times with 1×PBS and the wells aspirated to remove liquid.

250 μl of 0.2N NaOH containing 0.1 wt. % SDS was added to each well. The plate was wrapped in plastic and incubated at 65° C. for 60 min. The plate was then washed 3 times with 1×PBS and the wells aspirated to remove liquid.

100 μl of 50 mM sodium phosphate pH 7.8 with 0.4 mg/ml $BS^3$ was to each well and allowed to incubate with the plate for 12–18 hours. The plate was then washed 2 times with 1×PBS and 1 time with water. The plates were stored in plastic containers with desiccant at 4° C. The amplifier multimer was prepared as follows:

All chemical syntheses of oligonucleotides were performed on an automatic DNA synthesizer (Applied Biosystems, Inc., (ABI) model 380 B). Phosphoramidite chemistry of the β-cyanoethyl type was used including 5'-phosphorylation which employed PHOSTEL™ reagent (DMT—O—$CH_2CH_2$—($SO_2$)—$CH_2CH_2$—O—P(N(iPr)$_2$) (—O—$CH_2CH_2CN$) wherein DMT is dimethoxytrityl and iPr is isopropyl). Standard ABI protocols were used except as indicated. Where it is indicated that a multiple of a cycle was used (e.g., 1.2 cycle), the multiple of the standard amount of amidite recommended by ABI was employed in the specified cycle.

A comb body of the following structure was first prepared:

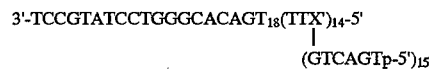

wherein X' is a branching monomer and p is a phosphate.

The portion of the comb body through the 14 (TTX') repeats was first synthesized using 33.8 mg aminopropyl-derivatized thymidine controlled pore glass (CPG) (2000 Å, 7.4 micromoles thymidine per gram support) with a 1.2 cycle protocol. The branching site nucleotide was of the formula:

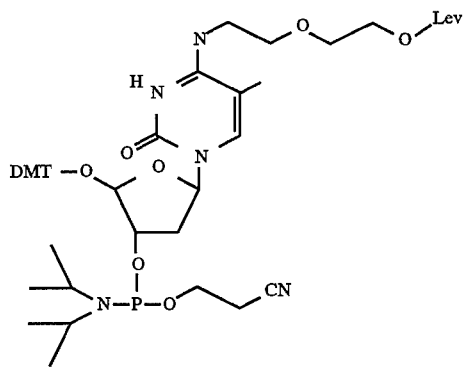

For synthesis of the comb body (not including sidechain extensions), the concentration of β-cyanoethylphosphoramidite monomers was 0.1M for A, C, G and T, and 0.15M for the branching site monomer X'. Detritylation was done with 3% trichloroacetic acid in methylene chloride using stepped flowthrough for the duration of the deprotection.

A six-base sidechain extension of the formula 3'-GTCAGTp was synthesized at each branching monomer site as follows. Two sidechain extensions were synthesized onto the terminal X' branching site. To remove the levulinyl group, a solution of 0.5M hydrazine hydrate in pyridine/glacial acetic acid (1:1 v/v) was introduced and kept in contact with the CPG support for 90 min with renewal of the liquid every 15 min, followed by extensive washing with pyridine/glacial acetic acid (1:1 v/v) and then by acetonitrile. After the deprotection the six base sidechain extensions were added using a 6.4 cycle.

In these syntheses the concentration of phosphoramidites was 0.1M (except 0.2M Phostel™ phosphorylating reagent).

Detritylation was effected with a solution of 3% trichloroacetic acid in methylene chloride using continuous flowthrough, followed by a rinse solution of toluene/chloromethane (1:1 v/v). Branched polynucleotide chains were removed from the solid supports automatically in the DNA synthesizer. The ammonium hydroxide solution was collected in 4 ml screw-capped Wheaton vials and heated at 60° C. for 12 hr to remove all base-protecting groups. After cooling to room temperature the solvent was removed in a Speed-Vac evaporator and the residue dissolved in 100 µl water. The sidechains and a ligation template/linker of the following structures were also made using the automatic synthesizer:

Sidechain:  SEQ ID NO: 21
3'-GATGCG(TTCATGCTGTTGGTGTAG)₃-5'(p)

Ligation template for linking sidechain extension:  SEQ ID NO: 22
3'-CGCATCACTGAC-5'(p)

The crude comb body was purified by a standard polyacrylamide gel (7% with 7M urea and 1× TBE running buffer) method.

The sidechains were ligated to the comb body as follows. The comb body (4 pmole/µl), sidechains (93.75 pmole/µl), and sidechain linking template (75 pmoles/µl) were combined in 1 mM ATP/5 mM DTT/50 mM Tris-HCl, pH 8.0/10 mM MgCl$_2$/2 mM spermidine. The mixture was heated in a water bath to 95° C., and then slowly cooled to below 35° C. over a 1 hr period. The concentrations of the components of the mixture were adjusted to 2 mM ATP, 10 mM DTT, 14% polyethylene glycol, then 0.2 units/µl T4 DNA ligase were added,. The mixture was incubated for 16–24 hr at 23° C. The DNA was precipitated in NaCl/ethanol and resuspended in water. Ligation products were then purified by polyacrylamide gel electrophoresis.

The hybridization assay was carried out as follows:

As a target, a synthetic 615 nucleotide transcript was prepared using a pGEM (Promega) vector containing nucleotides 54–668 of the HCV J1 clone and SP6 RNA polymerase. The negative control was no target.

Sample preparation consisted of delivering 200 µl of 2 mg/ml proteinase K in 0.07M Tris-HCl, pH 8.0/0.7M LiCl/0.06M sodium phosphate/0.06M EDTA, pH 7.0/0.7% SDS/50 fmoles capture extender probes (each)/200 fmole label extender probes (each)/5000 fmole competitor probes (each)) to each well. Different control experiments contained various combinations of the probes as indicated in the results table below. Plates were agitated to mix the contents in the well, covered and incubated for 16 hr at 63° C.

After a further 10 minute period at room temperature, the contents of each well were aspirated to remove all fluid, and the wells washed 2× with washing buffer (0.1% SDS/ 0.015M NaCl/0.0015M sodium citrate). The amplifier multimer was then added to each well (50 µl of 0.7 fmole/µl solution in 0.48M NaCl/0.048M sodium citrate/0.1% SDS/ 0.5% diethyl pyrocarbonate treated "blocking reagent" (a purified fraction of dry milk powder, Boehringer Mannheim, catalog No. 1096 176). After covering the plates and agitating to mix the contents in the wells, the plates were incubated for 30 min at 45° C.

After a further one minute period at room temperature, the wells were washed as described above.

Alkaline phosphatase label probe, disclosed in EP 883096976, was then added to each well (50 µl/well of 2.66 fmoles/µl). After incubation at 45° C. for 15 min, and 1 min at room temperature, the wells were washed three times as above and then three times with 0.015M NaCl/0.0015M sodium citrate.

An enzyme-triggered dioxetane (Schaap et al., *Tet. Lett.* 28:1159–1162 (1987) and EPA Pub. No. 0254051), obtained from Lumigen, Inc., was employed. 50 µl Lumiphos 530 (Lumigen) was added to each well. The wells were tapped lightly so that the reagent would fall to the bottom and gently swirled to distribute the reagent evenly over the bottom. The wells were covered and incubated at 37° C. for 20–40 min.

Plates were then read on a Dynatech ML 1000 luminometer. Output was given as the full integral of the light produced during the measurement period of 250 ms.

TABLE 1

| Line | Capture Extender | Competitor | Target | Relative Light Units (Std Dev) |
|---|---|---|---|---|
| 1 | No | No | No | 0.47 (0.08) |
| 2 | Yes | No | No | 0.47 (0.10) |
| 3 | Yes | Yes | No | 0.34 (0.01) |
| 4 | Yes | No | Yes | 38.0 (2.2) |
| 5 | Yes | Yes | Yes | 40.2 (7.1) |

With non-cruciform extenders, typically the "no capture extender" control has about 2-fold lower background than the control sample containing capture extenders. This is because molecules (LEs, AMP, and label) bind to the CEs. However, a comparison of line 1 and line 2 shows that the background with cruciform capture extenders is the same as the background without cruciform capture extenders. Comparison of lines 1, 2 and 3 shows that with competitor it is possible to reduce backgrounds below the level of the no capture extender control. Presumably this is due to blocking label extender binding to the capture probe. Comparison of lines 4 and 5 shows that competitors do not compete out target binding. Target binding is not affected by competitors because target is bound much more tightly via multiple CEs, which is much tighter than the binding of individual extender probes or individual competitors.

Example 2

Amplification Assay Using Multiple Label Extenders in a "Cruciform" Format

This example describes a hybridization assay using two different label extenders, as illustrated in FIG. 11. The goal of this experimental work was to reduce background signals caused by label extenders binding to the solid support or to the capture extender or capture probe molecules, i.e., the type of background which is generated when a label extender binds to the support in a manner not mediated by the target. Once the label extender is bound, the preamplifier, the amplifier multimer and the label probes (in this experiment, alkaline phosphatase label probes were used) can bind and generate signal that is not dependent on the presence of target. By reducing the ability of label extender probes to bind to the amplifier multimer individually, the preamplifier is forced to bind through multiple label extender probes in order to be bound stably to the surface. A preamplifier would not remain bound to a single label extender during the hybridization conditions of the assay. The label extenders are designed in a way where the two label extenders necessary to facilitate the binding of the amplifier multimer are located proximal to each other when they are bound to the target sequence. A single hybridized label extender will not efficiently bind preamplifier under the reaction conditions. In this way, the binding of the preamplifier is only favorable in the presence of target.

A synthetic oligonucleotide capture probe called PSCP (see Sequence #41) was attached to the plates. A set of HCV label extender probes were designed. Each label extender contains a sequence (T) complementary to the target in addition to one or two additional sequences (chosen from sequences A, B, C, or D) which bind to a preamplifier probe. This preamplifier contains sequences (A' and B', or C' and D') which bind to the LEs and eight repeats of a sequence (E') which binds the amplifier multimer.

A signal amplification solution phase nucleic acid sandwich hybridization assay format was employed in this example. The signal amplification is generated through a branched DNA multimer (amplifier) which is designed to have a first segment (E) that hybridizes to a segment of the preamplifier (E') and up to fifteen iterations of a segment (F), wherein segment F hybridizes to up to three alkaline phosphatase-labeled oligonucleotides. The target nucleic acid is bound to the solid support via capture probes and a plurality of capture extenders which hybridize to both the capture probes and the target. The capture extender probes, label extender probes and preamplifier probes as used in this assay were as follows.

Sequence (5'→3') Capture extender probes (the segment which binds to the immobilized capture probe is underlined):

20:
TCCTCACAGGGGAGTGATTCATGGTGGAGTGTC<u>CTCTTGGAAAGAAAGTGAAGTG</u> SEQ ID NO: 23
21:
ATGGCTAGACGCTTTCTGCGTGAAGACAGTAGT<u>CTCTTGGAAAGAAAGTGAAGTG</u> SEQ ID NO: 24
22:
TCCTGGAGGCTGCACGACRCTCATACTAACGCC<u>CTCTTGGAAAGAAAGTGAAGTG</u> SEQ ID NO: 25
23:
CGCAGACCACTATGGCTCTYCCGGGAGGGGGGG<u>CTCTTGGAAAGAAAGTGAAGTG</u> SEQ ID NO: 26
24:
TCRTCCYGGCAATTCCGGTGTACTCACCGGTTC<u>CTCTTGGAAAGAAAGTGAAGTG</u> SEQ ID NO: 27

Label extender probes used (the sequence which hybridizes to the target is underlined, the sequence as abbreviated above are enclosed in parentheses):

25: (A-T)
CTGAGTTTCTGGCTC<u>GCATTGAGCGGGTTDATCCAAGAAAGGACCCGG</u> SEQ ID NO: 28
26: (B-T-C)
ACTGAGTCAGTCAGTC<u>AGCAGTCTYGCGGGGGCACGCCCAARTCTCCAGGAAAGTTT GAATATG</u> SEQ ID NO: 29
27: (A-T-D)
CTGAGTTTCTGGCTC<u>ACAAGGCCTTTCGCAACCCAACACTACTCGGCTAC</u>CTACCTA CCTACCT SEQ ID NO: 30
28: (B-T-C)
AGTCAGTCAGTCAGTC<u>GGGGCACTCGCAAGCACCCTATCAGGCAGTACC</u>GAAAGTTT GAATATG SEQ ID NO: 31
29: (A-T-D)
CTGAGTTTCTGGCTC<u>YGTGCTCATGRTGCACGGTCTACGAGACCTCCC</u>ACCTACCTA CCTACCT SEQ ID NO: 32
30: (B-T-C)

```
AGTCAGTCAGTCAGTCGTTACGTTTGKTTYTTYTTTGRGGTTTRGGAWTGAAAGTTT
GAATATG SEQ ID NO: 33
31: (T-D)
CGGGAACTTRACGTCCTGTGGGCGRCGGTTGGTACCTACCTACCTACCT SEQ ID NO: 34
```

Label extender probes used for the control experiment were (the sequence which hybridizes to the target is underlined):

```
:HCV.33.13
AGGCATAGGACCCGTGTCTTCARGTAAACTCCACCRACGATCTGRCCRCCRCC SEQ ID NO: 35
:HCV.33.14
AGGCATAGGACCCGTGTCTTRCGCACACCCAAYCTRGGGCCCCTGCGCGGCAA SEQ ID NO: 36
:HCV.33.15
AGGCATAGGACCCGTGTCTTAGGTTGCGACCGCTCGGAAGTCTTYCTRGTCGC SEQ ID NO: 37
:HCV.33.16A
AGGCATAGGACCCGTGTCTTRCGHRCCTTGGGGATAGGCTGACGTCWACCTCG SEQ ID NO: 38
:HCV.33.16B
AGGCATAGGACCCGTGTCTTRCGHRCCTTGGGGATAGGTTGTCGCCWTCCACG SEQ ID NO: 39
:HCV.33.17
AGGCATAGGACCCGTGTCTTYCCRGGCTGRGCCCAGRYCCTRCCCTCGGRYYG SEQ ID NO: 40
:HCV.33.18
AGGCATAGGACCCGTGTCTTBSHRCCCTCRTTRCCRTAGAGGGGCCADGGRTA SEQ ID NO: 41
:HCV.33.19
AGGCATAGGACCCGTGTCTTGCCRCGGGGWGACAGGAGCCATCCYGCCCACCC SEQ ID NO: 42
:HCV.33.20
AGGCATAGGACCCGTGTCTTCCGGGGGTCYGTGGGGCCCCAYCTAGGCCGRGA SEQ ID NO: 43
:HCV.33.21
AGGCATAGGACCCGTGTCTTATCGATGACCTTACCCAARTTRCGCGACCTRCG SEQ ID NO: 44
:HCV.33.22
AGGCATAGGACCCGTGTCTTCCCCATGAGRTCGGCGAAGCCGCATGTRAGGGT SEQ ID NO: 45
32:
AGGCATAGGACCCGTGTCTTGCATTGAGCGGGTTDATCCAAGAAAGGACCCGG SEQ ID NO: 46
33:
AGGCATAGGACCCGTGTCTTAGCAGTCTYGCGGGGGCACGCCCAARTCTCCAG SEQ ID NO: 47
34:
AGGCATAGGACCCGTGTCTTACAAGGCCTTTCGCAACCCAACACTACTCGGCT SEQ ID NO: 48
35:
AGGCATAGGACCCGTGTCTTGGGGCACTCGCAAGCACCCTATCAGGCAGTACC SEQ ID NO: 49
36:
AGGCATAGGACCCGTGTCTTYGTGCTCATGRTGCACGGTCTACGAGACCTCCC SEQ ID NO: 50
37:
AGGCATAGGACCCGTGTCTTGTTACGTTTGKTTYTTYTTTGRGGTTTRGGAWT SEQ ID NO: 51
38:
AGGCATAGGACCCGTGTCTTCGGGAACTTRACGTCCTGTGGGCGRCGGTTGGT SEQ ID NO: 52
```

Preamplifier probes used (sequence E' is underlined, the starting and ending points for A', B', C', and D' are indicated by lowercase letters, the remaining sequences are for spacing):

```
39:
AGGCATAGGACCCGTGTCTTTTTTAGGCATAGGACCCGTGTCTTTTTTAGGCATAGG
ACCCGTGTCCGTGGATGTTTGAGGCATAGGACCCGTGTCTTTTTTAGGCATAGGACC
CGTGTCTTTTTTAGGCATAGGACCCGTGTCGCGTAGTGACTGAGGCATAGGACCCGT
GTCTTTTTTAGGCATAGGACCCGTGTCTTTTTTb'-CATATTCAAACTTTC-b'a'-
GAGCCAGAAACTCAGT-a' SEQ ID NO: 53
40:
AGGCATAGGACCCGTGTCTTTTTTAGGCATAGGACCCGTGTCTTTTTTAGGCATAGG
ACCCGTGTCCGTGGATGTTTGAGGCATAGGACCCGTGTCTTTTTTAGGCATAGGACC
CGTGTCTTTTTTAGGCATAGGACCCGTGTCGCGTAGTGACTGAGGCATAGGACCCGT
GTCTTTTTTAGGCATAGGACCCGTGTCTTTTTTd'-AGGTAGGTAGGTAGGT-d'
c'-GACTGACTGACTGACT-c' SEQ ID NO: 54
```

The plates used for the assay were coated as described above except instead of the DNA sequence CP2, the sequence PSCP was attached to the plate.

```
PSCP:
41:
5'- XCA CTT CAC TTT CTT TCC AAG AG-3' SEQ ID NO: 55
```

The amplifier multimer was prepared as described above. The hybridization assay was carried out as follows:

A standard curve of HCV was prepared by diluting a high titer hepatitis C virus sample in HCV negative human serum and delivering 50 μl aliquots of dilutions corresponding to a range of 1,500 to 19,500 viral equivalents to wells of microtiter dishes prepared as described above.

Sample preparation consisted of delivering 150 μl P-K Buffer (3.3 mg/ml proteinase K in 58 mM Tris-HCl, pH 8.0/0.6M NaCl/0.06M sodium citrate/12 mM EDTA, pH 8.0/1.3%SDS/16 μg/ml sonicated salmon sperm DNA/7% formamide/100 fmoles capture extender probes/400 fmoles label extender probes) to each well. The control experiment used 50 fmol/well capture extender probes, 160 fmol/well label extender probes in the same buffer. Plates were agitated to mix the contents in the well, covered and incubated for 16 hr at 63° C. The control experiment was left at 63° C. during the "preamplification" step.

After a further 10 minute period at room temperature, the contents of each well were aspirated to remove all fluid, and the wells washed 2× with washing buffer (0.1% SDS/ 0.015M NaCl/0.0015M sodium citrate). The preamplifier probes were then added (100 fmole in 50 μl 0.75M NaCl/ 0.075M sodium citrate/0.1% SDS/0.5% blocking reagent (as above, Boehringer Mannheim, catalog No. 1096 176)) to each well (except control). Plates were agitated, covered and incubated at 53° C. for 30 min.

The plates were then cooled and washed as described above. The amplifier multimer was then added to each well (85 fmol in same buffer used for preamplifier probes). The control experiment used 30 fmol/well amplifier multimer in the same buffer. After covering the plates and agitating to mix the contents in the wells, the plates were incubated for 30 min at 53° C.

After a further 10 min period at room temperature, the wells were washed as described above.

Alkaline phosphatase label probe, disclosed in EP 883096976, was then added to each well (125 fmol in 50 μl 0.75M NaCl/0.075M sodium citrate/0.1% SDS/0.5% blocking reagent (as above, Boehringer Mannheim, catalog No. 1096 176)). After incubation at 53° C. for 15 min, and 10 min at room temperature, the wells were washed twice as above and then 3× with 0.015M NaCl/0.0015M sodium citrate.

An enzyme-triggered dioxetane (Schaap et al., Tet. Lett. (1987) 28:1159–1162 and EPA Pub. No. 0254051), obtained from Lumigen, Inc., was used as the luminescence substrate. 50 μl Lumiphos 530 (Lumigen) was added to each well. The wells were covered, agitated for 30 sec and incubated at 37° C. for 25 min.

Plates were then read on a Dynatech ML 1000 luminometer. Output was given as the full integral of the light produced during the 250 millisec read time.

Results are shown in the Table below.

| Target Concentration | With Preamplifiers (Relative Light Units) | Without Preamplifiers (Relative Light Units) |
| --- | --- | --- |
| 1 | 3.87 (±0.26) | 1.58 (±0.15) |
| 2 | 1.64 (±0.15) | 0.80 (±0.09) |
| 3 | 1.08 (±0.16) | 0.61 (±0.09) |
| 0 | 0.63 (±0.05) | 0.43 (±0.04) |

The assay run with preamplifier probes had a higher value for signal minus noise for each of the analyte concentrations compared to the assay run without preamplifier probes.

Example 3
Multidentate Capture

In this example, $T_m$ measurements were carried out on microwells containing the capture probe xtl* (see U.S. patent application Ser. No. 07/813,588, cited earlier herein, and EPA 883096976). Capture extenders and the xtl* capture probe were as follows:

xtl-tailed HCV capture extenders (5'→3'; functional domains of the probes are separated by periods):

```
:HCV.33.1.XT1:
TCCTCACAGGGGAGTGATTCATGGTGGAGTGTC.CTTCTTTGGAGAAAGTGGTG SEQ ID NO: 56
:HCV.33.2.XT1:
ATGGCTAGACGCTTTCTGCGTGAAGACAGTAGT.CTTCTTTGGAGAAAGTGGTG SEQ ID NO: 57
:HCV.33.3.XT1:
GCCTGGAGGCTGCACGRCACTCATACTAACGCC.CTTCTTTGGAGAAAGTGGTG SEQ ID NO: 58
:HCV.33.4.XT1:
CGCAGACCACTATGGCTCTYCCGGGAGGGGGGG.CTTCTTTGGAGAAAGTGGTG SEQ ID NO: 59
:HCV.33.5.XT1:
TCRTCCYGGCAATTCCGGTGTACTCACCGGTTC.CTTCTTTGGAGAAAGTGGTG SEQ ID NO: 60
xtl* capture probe:
CACCACTTTCTCCAAAGAAG SEQ ID NO: 61
```

Capture extender probes and HCV target RNA were labeled with P-32. For the capture extender-capture probe $T_m$ determination, labeled capture extenders were equilibrated with xtl* wells at various temperatures or in the presence of various levels of the denaturant formamide. Either two hours or overnight equilibration was used. For the capture extenders-target-capture probe $T_m$ determination, the capture extenders were hybridized to P-32 labeled target. The capture extenders-target complex was then equilibrated with the capture probe wells either two hours or overnight at the various temperatures. Samples were drawn off the microwells at temperature and the percent binding determined. The $T_m$ or $C_m$ were determined as the midpoints of the curves with percent binding plotted against temperature or percent formamide. To convert $C_m$ (formamide) to $T_m$ (no formamide), the fact that each percent formamide lowers the $T_m$ by 0.7 degrees was used.

Figure 14:
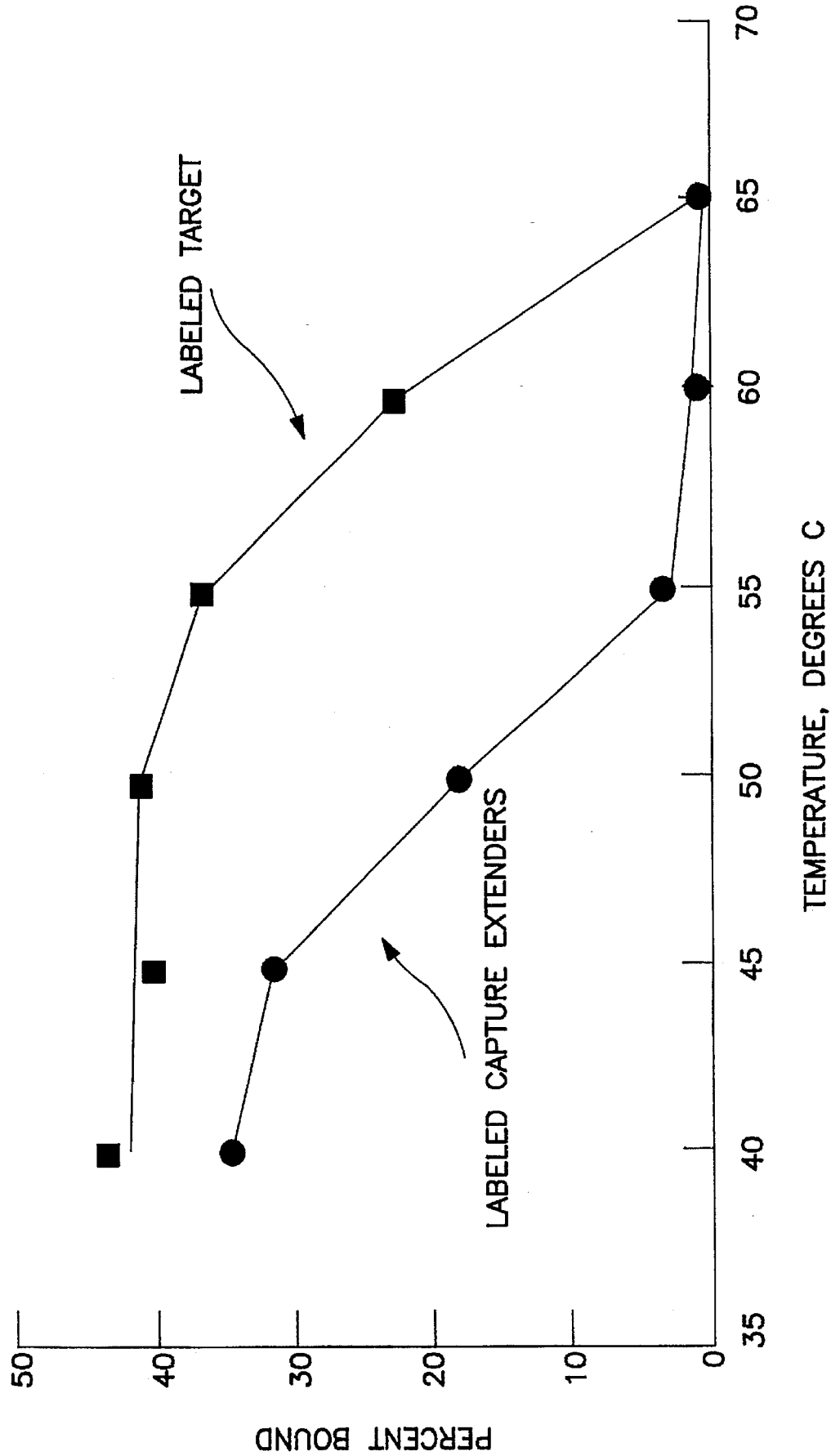
FIG. 14 shows the melting curves of capture extenders-labeled target-capture probe and labeled capture extenders-capture probe with 2 hours equilibration.

The melting curves of capture extenders-labeled target-xtl* capture probe and labeled capture extenders-xtl* capture probe with 2 hours equilibration are shown in FIG. 14. The melting temperatures in 20% formamide and 0.6M LiCl are: 50 degrees for capture extenders-xtl* and 60 degrees for capture extenders-target-xtl*. These numbers correspond to $T_m$ values of 64 and 74 degrees in the absence of formamide. FIG. 14 shows that 36% of the target and only 2% of the capture extenders are bound at 55 degrees in 20% formamide. This is an 18× difference that is based on target capture through multiple capture extenders.

One skilled in the art will appreciate that the difference in $T_m$ between the target-capture extender-capture probe complex and capture extender-capture probe complex can be increased beyond 10 degrees. By lowering the capture extender-capture probe $T_m$, one will magnify the effect of multidentate binding.

Example 4

Hybridization Assay Using Two Amplifiers

From the previous examples it is clear that probes can be designed such that multiple (two or more) interactions are required to achieve a stable complex under the conditions of the assay. The term multiple interactions is not intended to be limiting in any way. Two types of multiple interactions have been illustrated: multiple probes forming a cruciform (4-way branched) junction and multiple capture extenders simultaneously binding to multiple capture probes on a solid support, resulting in the Target-solid support $T_m$ being 10–20 degrees higher than the $T_m$ of a single capture extender-capture probe hybrid.

Figure 15:
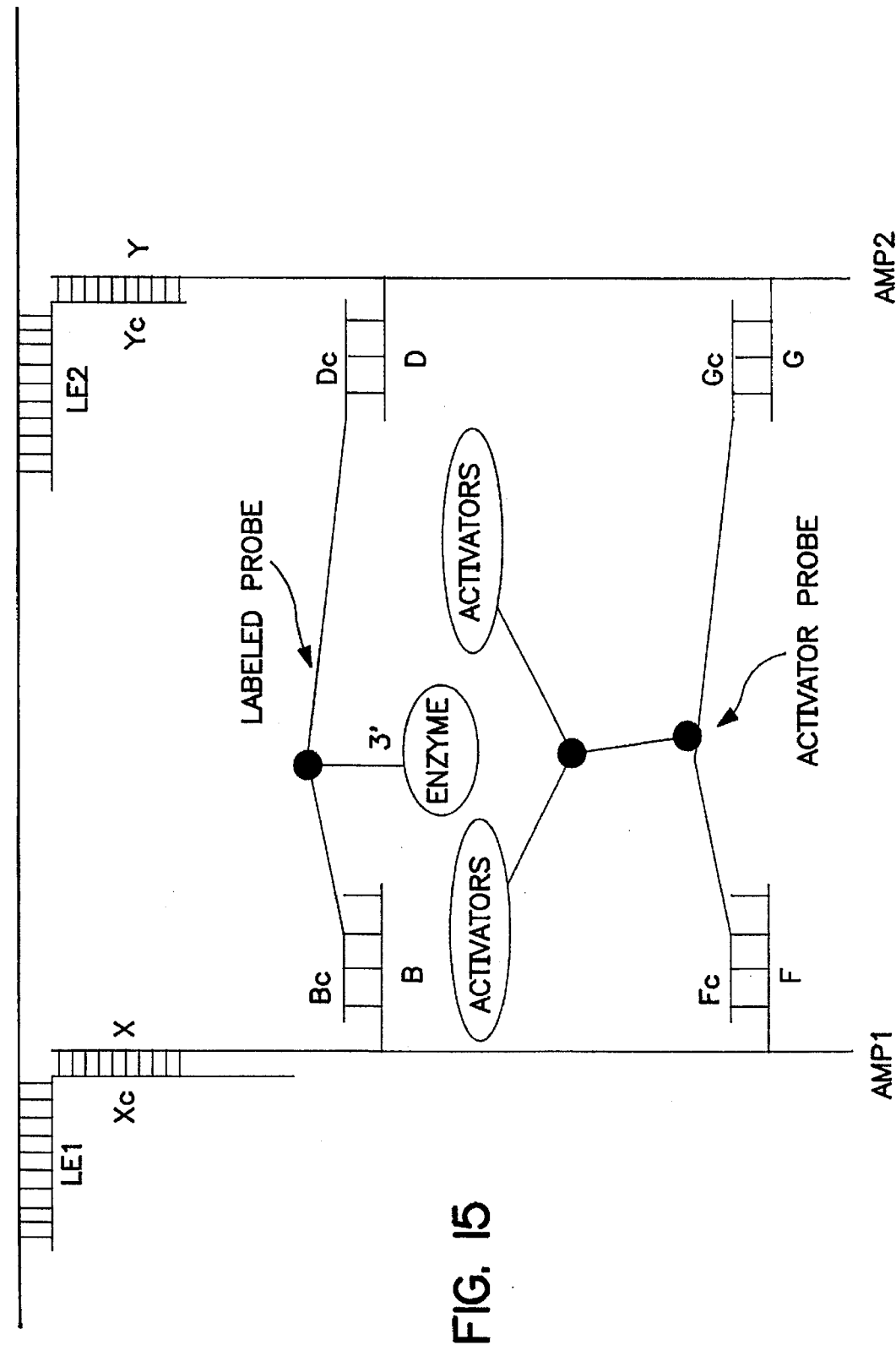
FIG. 15 is another example of the improved nucleic acid hybridization assay of the present invention using multiple amplification multimers and multiple bridging label probes.

The same concepts are extended to multiple amplifiers. A workable probe design is shown in FIG. 15. In this instance two branched DNA amplifiers are bound to two label extenders. Amp1 is bound to label extender LE1 through the stable hybrid sequence X. Amp2 is bound to label-extender LE2 through stable hybrid sequence Y. LE1 and LE2 do not have to be contiguous, but both must be bound to non-overlapping regions of the same target molecule. AMP1 contains branching sequences B and F and amp 2 contains branching sequences D and G. In this example, an enzyme-labeled probe contains sequences Bc and Dc, while an activator probe contains sequences Fc and Gc. In FIG. 15 label extenders form stable hybrids with target and with their respective amplifiers. All other hybrids shown (involving B, D, F, G) are designed to be too weak to form stable hybrids at the temperature of the hybridization. The weak hybrids are designed to have melting temperatures about 10–20 degrees below the assay hybridization temperature. A design with melting temperatures 5 degrees below the assay temperature is also acceptable. The preferable difference is 10–20 degrees since this can increase target specific binding by 100–1000 fold.

In this way, for example, when an enzyme-labeled probe binds to sequence B, it quickly dissociates unless sequence D is nearby as well. Once a probe binds to both AMP1 and AMP2, the conformation becomes more fixed in space, kinetically favoring the next binding event. The activator probe binds independently of the labeled probe but in like manner. The binding of the activator probe is kinetically but not thermodynamically favored by the binding of the labeled probe to AMP1 and AMP2 and vice versa.

The activator probe(s) can take many forms. They can (1) activate the enzymes directly or (2) activate the enzymes indirectly by relieving inhibition or (3) they can activate the detection of the product of the enzyme reaction. As an example of method (3), the enzyme in the enzyme-labeled probe could be alkaline phosphatase and the activators could be a fluoresceinated polymer similar in composition and structure to that disclosed by Schaap et al., in *Clinical Chemistry* 35:1863–1864 (1989). In the presence of this polymer the light output from the dephosphorylated dioxetane increased 400-fold. Ideally the luminescence activators would sandwich the enzyme-labeled probes so that dioxetane released by the enzyme would have a high probability of transferring energy to the fluorescein or other luminescent enhancers for efficient target-dependent light emission. The conditions chosen for the detection step would favor a very short lifetime of the dioxetane, reducing the efficiency of detection of dioxetane in the absence of enhancer-labeled target. By removing the fluorescein polymers or other luminescence enhancers from the bulk phosphorylated dioxetane substrate mixture, the signal will be made much more target-dependent. Even an alkaline phosphatase bound nonspecfically to the solid support that cleaves a phosphorylated dioxetane will most likely not be detected unless it survives long enough to diffuse to the target. By this method even background is converted into a type of signal (i.e. the presence of target will be required to see most of the noise).

The activator probes could also be enzyme-activators or moieties that relieve enzyme inhibition. The enzyme could have two or more subunits. Ideally it would be engineered so that the natural affinity of the subunits would be reduced or removed. In place of the amino acids responsible for the natural association would be very short oligonucleotide sequences (sequence H on one subunit and the complementary sequence Hc on the other subunit) that cannot form a stable hybrid by themselves but which would be capable of associating the two inactive subunits and thus forming an active complex if the subunits were held close to one another by virtue of a target molecule's binding both subunits to different branches of two different amplifiers as in FIG. 15.

An example of activation by means of relieving enzyme inhibition would be as follows. The labeled oligonucleotide would be covalently bound to both alkaline phosphatase and theophylline, or other non-competitive enzyme inhibitor. The activator probe would contain an anti-theophylline antibody with a Ka much higher than the 1/Ki of theophylline for alkaline phosphatase. The oligo probe containing the anti-theophylline antibody would be added in the presence of sufficient reversible denaturant such that the activator will not bind to the enzyme inhibitor. Examples of such reversible denaturants include formamide and urea, which alkaline phosphatase tolerates very well. The wash steps would remove the denaturant along with the excess activator and labeled probes. At which time the target-bound anti-theophylline antibody, by virtue of its proximity, would bind theophylline because Ka>>1/Ki and thus relieve the inhibition of the alkaline phosphatase. Solid-support bound alkaline phosphatase would remain inhibited by the theophylline tethered to the labeled probe because non-specifically bound anti-theophylline antibody is not close enough to relieve the inhibition.

A three-part system may also be constructed, in which branched DNA amplifiers with at least three short sequences such that two enzyme subunits (whose natural affinity for each other has been reduced or removed) are brought into proximity and they are in turn surrounded by luminescent activators. In addition, a branched DNA amplifier bringing one subunit of an enzyme and another branched DNA amplifier (bound to another label extender) bringing in the other subunit or an activator can be used. In addition it is equally possible to use linear amplifiers containing many different consecutive sequences to support bridging molecules. Such linear amplifiers can be easily made by ligation as discussed earlier.

Example 5

A Hybridization Assay Combining the Concepts

The goal of the present invention is to reduce the background noise in hybridization assays. By drastically reducing the binding of capture extenders to the solid support, the background due to molecules that bind the capture extenders is reduced. By binding an amplifier through two label extenders, background is reduced because a label extender binding to either the solid support or to any molecule bound to the solid support (including capture probe and capture extenders) is not efficiently labeled. Similarly, an amplifier that binds to the support in the absence of target is not efficiently labeled if it forms a hybrid with the labeled probe having a $T_m$ 10–20 degrees below the assay temperature. Also, a labeled probe that binds to the solid support or any molecule bound to the solid support is inefficiently detected if that labeled probe is not activated by its cofactors or other subunits. Activators of luminescence can increase light output more than one hundred fold (Schaap et al., supra). If the activator is removed from the substrate solution and instead bound to the target, there is a significant opportunity for noise reduction in the hybridization assay.

Figure 16:
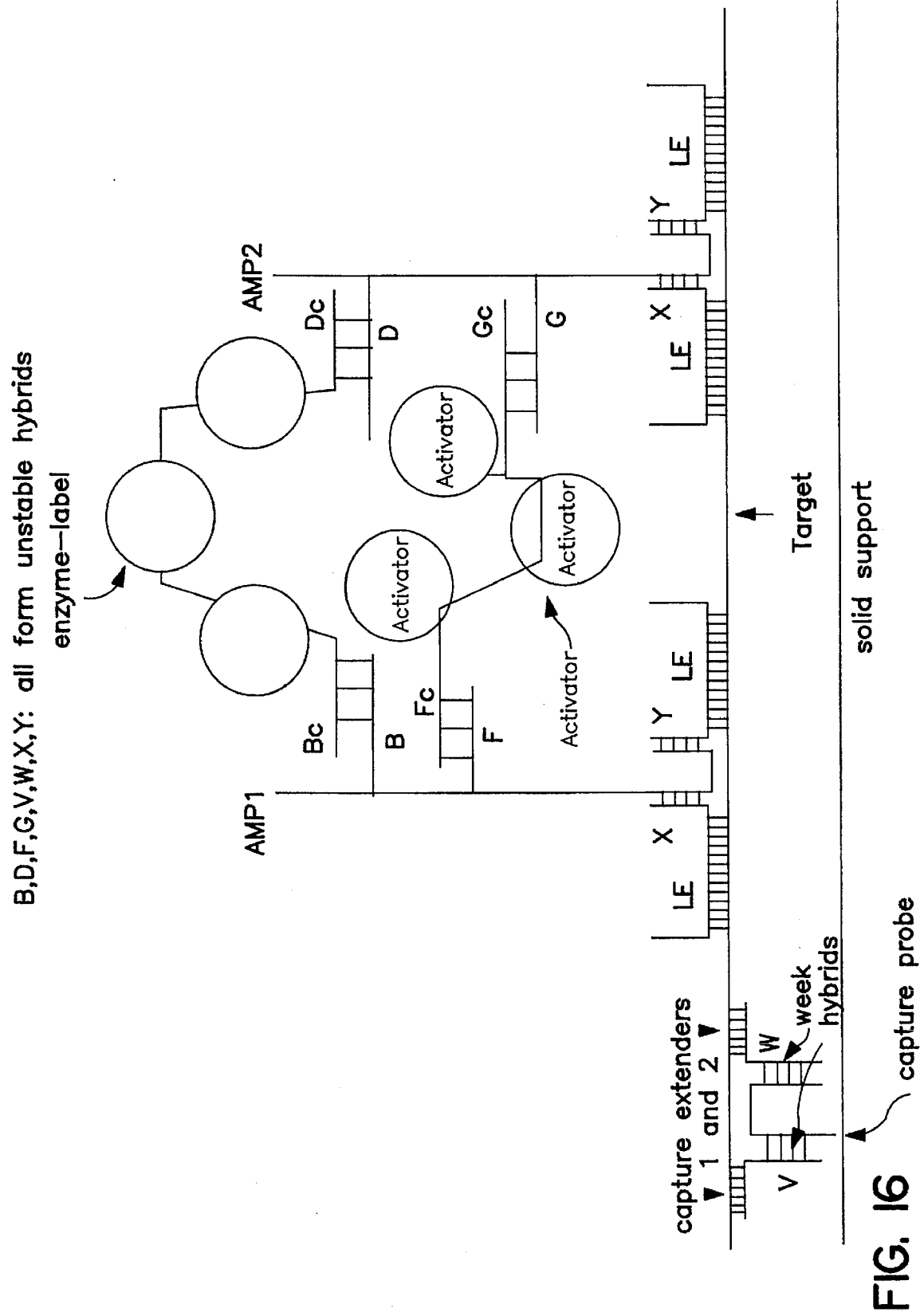
FIG. 16 is an example of the improved nucleic acid hybridization assay of the present invention combining several of the individual concepts disclosed herein.

The present example describes how to use these concepts in a single assay. Use of any one concept results in a detectable decrease in background. Use of all of them can in principle make background undetectable, permitting the use of stronger signal amplification to increase sensitivity. A workable probe design combining these concepts is shown in FIG. 16. Capture extenders and label extenders can be designed to hybridize simultaneously to the target in cruciforms. The $T_m$ of the target binding region of the extenders is designed to be more than about 10 degrees more stable than that of hybrids involving sequences V and W and X and Y. The $T_m$ of the capture probe—target complex is designed to be about 10 degrees or more stable than the capture extender—capture probe complex. During the hybridization a vast molar excess of the sequences 'V' and 'W' may be included to further reduce capture extender binding to the solid support (especially in case a cool down step is included after hybridization). As shown previously, the 'V' and 'W' sequences have no effect on the target binding.

After capture is complete, an optional washing cycle is done to remove excess probes. Then, as illustrated in FIG. 16, enzyme-labeled probes containing short sequences Bc and Dc and an optional activator probe containing sequences Fc and Gc are added and hybridization conducted at a temperature approximately 20 degrees higher than the $T_m$s of hybrids involving sequences B, D, F, G. For example, the $T_m$s of sequences B, D, F, and G could be designed to be 35 degrees, while the hybridization temperature could be 50 degrees and the $T_m$s of the complexes formed with AMP1 and AMP2 could be 55 to 60 degrees. Alternatively, the hybridization could be done at approximately 37 degrees in the presence of sufficient protein denaturant to (1) reduce or effectively prevent association of activator and enzyme and (2) to reduce or effectively prevent binding of labeled probe and/or activator to just one amplifier (that is, to increase the effective hybridization temperature to approximately 50 degrees). Preferably, protein engineering would be used to minimize interactions between enzyme and enzyme activator(s). Finally, the solid support is washed and detection is done. The preferred substrate would be a phosphorylated dioxetane. No enhancer would be present in this substrate mix, since ideally the enhancers are bound to the target. That is, either the activator of FIG. 16 is itself a luminescence activator or luminescence activators are included in the hybridization with the enzyme activators and enzyme-labeled oligonucleotide probes.

We claim:

1. In a solution phase sandwich hybridization assay for detecting a nucleic acid analyte in a sample, comprising: (a) binding the analyte indirectly to a solid support; (b) labelling the analyte; (c) detecting the presence of label on the support; and (d) correlating the presence of the label on the support with the presence of the nucleic acid analyte in the sample, the improvement which comprises incorporating a first capture extender molecule and a distinct second capture extender molecule into the assay both of which must hybridize to the analyte in order for the assay to result in the detectable signal, said first and second capture extender molecules each comprising a polynucleotide containing an analyte-binding segment capable of hybridizing to a nucleic acid sequence present in the analyte and a support-binding segment capable of hybridizing to a nucleic acid sequence present within a capture probe bound to a solid support, wherein the analyte-binding segment of the first capture extender molecule is distinct from the analyte-binding segment of the second capture extender molecule, and further wherein the capture probe contains a first capture extender binding sequence capable of hybridizing to the support-binding segment of the first capture extender molecule, and a second capture extender binding sequence capable of hybridizing to the support-binding segment of the second capture extender molecule, such that two distinct capture extender molecules can bind to a single capture probe.

2. The assay of claim 1, wherein the melt temperature $T_{m1}$ at which the nucleic acid analyte dissociates from the capture probe in the hybrid complex formed between the capture probe, capture extender molecules and nucleic acid analyte is at least about 5° C. greater than the melt temperature $T_{m2}$ of hybrid complexes formed between the capture probe and capture extender molecules.

3. The assay of claim 2 wherein at least one step is carried out under stringency conditions which favor the $T_{m1}$ complex formation, but disfavor the $T_{m2}$ complex formation.

4. The assay of claim 3 wherein stringency is controlled by controlling at least one step parameter selected from the group consisting of formamide concentration, chaotropic salt concentration, salt concentration, pH (hydrogen ion concentration), organic solvent content, and temperature.

5. The assay of claim 4 wherein the at least one step is carried out at a temperature greater than $T_{m2}$ and less than $T_{m1}$.

6. The assay of claim 3 wherein the at least one step comprises step (a).

7. A solution phase sandwich hybridization assay for detecting the presence of a nucleic acid analyte in a sample, comprising:

(a) providing a solid support having capture probes thereon, capture extender molecules having a first segment C-1 capable of hybridizing to a nucleic acid sequence in the analyte and a second segment C-2 capable of hybridizing to a nucleic acid sequence in the capture probes, label extender molecules having a first segment L-1 capable of hybridizing to a nucleic acid sequence in the analyte and a second segment L-2 capable of hybridizing to a label probe system, a label probe system comprising a nucleic acid sequence M-1 capable of hybridizing to L-2 and which, directly or indirectly, gives rise to a detectable signal;

(b) incubating the nucleic acid analyte under hybridization conditions with the capture extender molecules at least two of which must hybridize to the analyte in order for the assay to result in a detectable signal, label extender molecules, and the capture probes on the solid support, simultaneously or sequentially in any order, to form a support-bound hybrid complex;

(c) thereafter optionally separating materials not bound to the solid support;

(d) thereafter contacting the support-bound hybrid complex with the label probe system under hybridizing conditions, to provide a labeled, support-bound hybrid complex;

(e) thereafter separating materials not bound to the solid support;

(f) detecting the presence of label in the support-bound hybrid complex; and (g) correlating the presence of the label in the support-bound hybrid complex with the presence of the nucleic acid analyte in the sample, wherein the melt temperature $T_{m1}$ at which the nucleic acid analyte dissociates from the capture probe in the hybrid complex formed between the capture probe, capture extender molecules and nucleic acid analyte is at least about 5° C. greater than the melt temperature $T_{m2}$ of hybrid complexes formed between the capture probe and capture extender molecules.

8. The assay of claim 7, wherein the label probe system comprises (i) an amplification multimer containing the nucleic acid sequence M-1 and a plurality of identical oligonucleotide subunits containing nucleic acid sequences M-2 capable of hybridizing to label probes, and (ii) label probes containing a nucleic acids sequence L-3 which is capable of hybridizing to M-2 and which, directly or indirectly, gives rise to a detectable signal, and wherein step (d) of the assay comprises the following steps:

($d_1$) contacting the support-bound hybrid complex under hybridizing conditions with the amplification multimer, to produce a second support-bound hybrid complex;

($d_2$) thereafter optionally separating materials not bound to the solid support; and ($d_3$) thereafter contacting the second support-bound hybrid complex with the label probes under hybridization conditions, to produce a labeled support-bound hybrid complex.

9. The assay of claim 7, wherein at least one step is carried out under stringency conditions which favor the $T_{m1}$ complex formation, but disfavor the $T_{m2}$ complex formation.

10. The assay of claim 9 wherein stringency is controlled by controlling at least one step parameter selected from the group consisting of formamide concentration, chaotropic salt concentration, salt concentration, pH (hydrogen ion concentration), organic solvent content, and temperature.

11. The assay of claim 10 wherein the at least one step is carried out at a temperature greater than $T_{m2}$ and less than $T_{m1}$.

12. The assay of claim 9 wherein the at least one step comprises step (b).

13. A solution phase sandwich hybridization assay for detecting the presence of a nucleic acid analyte in a sample, comprising:

(a) providing a solid support having capture probes thereon, capture extender molecules having a first segment C-1 capable of hybridizing to a nucleic acid sequence in the analyte and a second segment C-2 capable of hybridizing to a nucleic acid sequence in the capture probes, label extender molecules having a first segment L-1 capable of hybridizing to a nucleic acid sequence in the analyte and a second segment L-2 capable of hybridizing to a nucleic acid sequence P-1 in a preamplifier probe, a preamplifier probe having a nucleic acid sequence P-1 and capable of binding a plurality of amplification multimers through nucleic acid sequences P-2, amplification multimers containing a nucleic acid sequence M-1 capable of hybridizing to P-2 and a plurality of identical oligonucleotide subunits containing nucleic acid sequences M-2 capable of hybridizing to label probes, and label probes containing a sequence L-3 which is capable of hybridizing to M-2 and which, directly or indirectly, gives rise to a detectable signal;

(b) incubating the nucleic acid analyte under hybridization conditions with the capture extender molecules at least two of which must hybridize to the analyte in order for the assay to result in a detectable signal, label extender molecules, and the capture probes on the solid support, simultaneously or sequentially in any order, to form a support-bound, first hybrid complex;

(c) thereafter optionally separating materials not bound to the solid support;

(d) contacting the support-bound, first hybrid complex under hybridization conditions with the preamplifier probe and the amplification multimer, to produce a support-bound, second hybrid complex;

(e) thereafter optionally separating materials not bound to the solid support;

(f) contacting the support-bound, second hybrid complex with the label probes under hybridizing conditions, to produce a labeled, support-bound, third hybrid complex;

(g) thereafter separating materials not bound to the solid support;

(h) detecting the presence of label in the support-bound, third hybrid complex; and (i) correlating the presence of the label in the support-bound, third hybrid complex with the presence of the nucleic acid analyte in the sample, wherein the melt temperature $T_{m1}$ at which the nucleic acid analyte dissociates from the capture probe in the hybrid complex formed between the capture probe, capture extender molecules and nucleic acid analyte is at least about 5° C. greater than the melt temperature $T_{m2}$ of hybrid complexes formed between the capture probe and capture extender molecules.

14. A solution phase sandwich hybridization assay for detecting the presence of a nucleic acid analyte in a sample, comprising:

(a) providing a solid support having capture probes thereon, a first capture extender molecule comprising a polynucleotide containing an analyte-binding segment capable of hybridizing to a nucleic acid sequence present in the analyte and a support-binding segment capable of hybridizing to a nucleic acid sequence present within the capture probes, a distinct second capture extender molecule comprising a polynucleotide containing an analyte-binding segment capable of hybridizing to a nucleic acid sequence present in the analyte and a support-binding segment capable of hybridizing to a nucleic acid sequence present within the capture probes, label extender molecules having a first segment L-1 capable of hybridizing to a nucleic acid sequence in the analyte and a second segment L-2, an amplification multimer containing a nucleic acid sequence M-1 capable of hybridizing to L-2 and a plurality of identical oligonucleotide subunits containing nucleic acid sequences M-2, and label probes containing a sequence L-3 which is capable of hybridizing to M-2 and which, directly or indirectly, gives rise to a detectable signal;

(b) incubating the nucleic acid analyte under hybridization conditions with the capture extender molecules, label extender molecules, and the capture probes on the solid support, simultaneously or sequentially in any order, to form a support-bound, first hybrid complex;

(c) thereafter optionally separating materials not bound to the solid support;

(d) contacting the support-bound, first hybrid complex under hybridization conditions with the amplification multimer, to produce a support-bound, second hybrid complex;

(e) thereafter optionally separating materials not bound to the solid support;

(f) contacting the support-bound, second hybrid complex with the label probes under hybridizing conditions, to produce a labeled, support-bound, third hybrid complex;

(g) thereafter separating materials not bound to the solid support;

(h) detecting the presence of label in the support-bound, third hybrid complex; and (i) correlating the presence of the label in the support-bound, third hybrid complex with the presence of the nucleic acid analyte in the sample, wherein the capture extender molecules are configured such that the support-bound, second hybrid complex of step (b) will form only when both first and second capture extender molecules have bound to the analyte.

15. A solution phase sandwich hybridization assay for detecting the presence of a nucleic acid analyte in a sample, comprising:

(a) providing a solid support having capture probes thereon, a first capture extender molecule comprising a polynucleotide containing an analyte-binding segment capable of hybridizing to a nucleic acid sequence present in the analyte and a support-binding segment capable of hybridizing to a nucleic acid sequence present within the capture probes, a distinct second capture extender molecule comprising a polynucleotide containing an analyte-binding segment capable of hybridizing to a nucleic acid sequence present in the analyte and a support-binding segment capable of hybridizing to a nucleic acid sequence present within the capture probes, label extender molecules having a first segment L-1 capable of hybridizing to a nucleic acid sequence in the analyte and a second segment L-2 capable of hybridizing to a nucleic acid sequence P-1 in a preamplifier probe, a preamplifier probe having the nucleic acid sequence P-1 and capable of binding a plurality of amplification multimers through nucleic acid sequences P-2, amplification multimers containing a nucleic acid sequence M-1 capable of hybridizing to P-2 and a plurality of identical oligonucleotide subunits containing nucleic acid sequences M-2 capable of hybridizing to label probes, and label probes containing a sequence L-3 which is capable of hybridizing to M-2 and which, directly or indirectly, gives rise to a detectable signal;

(b) incubating the nucleic acid analyte under hybridization conditions with the capture extender molecules, label extender molecules, and the capture probes on the solid support, simultaneously or sequentially in any order, to form a support-bound, first hybrid complex;

(c) thereafter optionally separating materials not bound to the solid support;

(d) contacting the support-bound, first hybrid complex under hybridization conditions with the preamplifier probe and the amplification multimer, to produce a support-bound, second hybrid complex;

(e) thereafter optionally separating materials not bound to the solid support;

(f) contacting the support-bound, second hybrid complex with the label probes under hybridizing conditions, to produce a labeled, support-bound, third hybrid complex; and (h) thereafter separating materials not bound to the solid support;

(i) detecting the presence of label in the support-bound, third hybrid complex; and (j) correlating the presence of the label in the support-bound, third hybrid complex with the presence of the nucleic acid analyte in the sample, wherein the capture extender molecules are configured such that the support-bound, second hybrid complex of step (b) will form only when both first and second capture extender molecules have bound to the analyte.

16. The assay of claim 14, wherein the capture probe contains a first capture extender binding sequence capable of hybridizing to the support-binding segment of the first capture extender molecule, and a second capture extender binding sequence capable of hybridizing to the support-binding segment of the second capture extender molecule, such that two capture extender molecules can bind to a single capture probe.

17. The assay of claim 15, wherein the capture probe contains a first capture extender binding sequence capable of hybridizing to the support-binding segment of the first capture extender molecule, and a second capture extender binding sequence capable of hybridizing to the support-binding segment of the second capture extender molecule, such that two capture extender molecules can bind to a single capture probe.

18. A solution phase sandwich hybridization assay for detecting the presence of a nucleic acid analyte in a sample, comprising:

(a) providing a solid support having capture probes thereon, capture extender molecules comprising polynucleotides containing an analyte-binding segment capable of hybridizing to a nucleic acid sequence present in the analyte and a support-binding segment capable of hybridizing to a nucleic acid sequence present within the capture probes, a first label extender molecule having a first segment capable of hybridizing to a nucleic acid sequence in the analyte and a second segment capable of hybridizing to a label probe system, a distinct second label extender molecule having a first segment capable of hybridizing to a nucleic acid sequence in the analyte and a second segment capable of hybridizing to a label probe system, a label probe system comprising nucleic acid sequences capable of hybridizing to the second segments of the first label extender molecule and the second label extender molecule, and which, directly or indirectly, gives rise to a detectable signal;

(b) incubating the nucleic acid analyte under hybridization conditions with the capture extender molecules, label extender molecules and the capture probes on the solid support, simultaneously or sequentially in any order, to form a support-bound hybrid complex;

(c) thereafter optionally separating materials not bound to the solid support;

(d) thereafter contacting the support-bound hybrid complex with the label probe system under hybridizing condition, to produce a labeled, support-bound hybrid complex; and (e) thereafter separating materials not bound to the solid support;

(f) detecting the presence of label in the labeled support-bound hybrid complex; and (g) correlating the presence of the label in the support-bound, third hybrid complex with the presence of the nucleic acid analyte in the sample, wherein the label extender molecules are configured such that the support-bound, third hybrid complex of step (d) will form only when both first and second label extender molecules have bound to the analyte.

19. The assay of claim 18, wherein the label probe system comprises (i) an amplification multimer containing the nucleic acid sequence M-1 and a plurality of identical oligonucleotide subunits containing nucleic acid sequences M-2 capable of hybridizing to label probes, and (ii) label probes containing a nucleic acids sequence L-3 which is capable of hybridizing to M-2 and which, directly or indirectly, gives rise to a detectable signal, and wherein step (d) of the assay comprises the following steps:

($d_1$) contacting the support-bound hybrid complex under hybridizing conditions with the amplification multimer, to produce a second support-bound hybrid complex;

($d_2$) thereafter optionally separating materials not bound to the solid support; and ($d_3$) thereafter contacting the second support-bound hybrid complex with the label probes under hybridization conditions, to produce a labeled support-bound hybrid complex.

20. A solution phase sandwich hybridization assay for detecting the presence of a nucleic acid analyte in a sample, comprising:

(a) providing a solid support having capture probes thereon, capture extender molecules comprising polynucleotides containing an analyte-binding segment capable of hybridizing to a nucleic acid sequence present in the analyte and a support-binding segment capable of hybridizing to a nucleic acid sequence present within the capture probes, a first label extender molecule having a first segment capable of hybridizing to a nucleic acid sequence in the analyte and a second segment capable of hybridizing to a preamplifier probe, a distinct second label extender molecule having a first segment capable of hybridizing to a nucleic acid sequence in the analyte and a second segment capable of hybridizing to a preamplifier probe, preamplifier probes having a first segment capable of hybridizing to a label extender molecule and a second segment capable of binding a plurality of amplification multimers, amplification multimers containing a nucleic acid sequence M-1 capable of hybridizing to the label extender molecules and containing a plurality of identical oligonucleotide subunits containing nucleic acid sequences M-2, and label probes containing a sequence which is capable of hybridizing to M-2 and which, directly or indirectly, gives rise to a detectable signal;

(b) incubating the nucleic acid analyte under hybridization conditions with the capture extender molecules, label extender molecules, and the capture probes on the solid support, simultaneously or sequentially in any order, to form a support-bound, first hybrid complex;

(c) thereafter optionally separating materials not bound to the solid support;

(d) contacting the support-bound, first hybrid complex under hybridization conditions with the preamplifier probe and the amplification multimers, to produce a support-bound, second hybrid complex;

(e) thereafter optionally separating materials not bound to the solid support;

(f) contacting the support-bound, second hybrid complex with the label probes under hybridizing conditions, to produce a labeled, support-bound, third hybrid complex; and (g) thereafter separating materials not bound to the solid support;

(h) detecting the presence of label in the support-bound, third hybrid complex; and (i) correlating the presence of the label in the support-bound, third hybrid complex with the presence of the nucleic acid analyte in the sample, wherein the label extender molecules are configured such that the support-bound, second hybrid complex of step (d) will form only when both first and second label extender molecules have bound to the analyte.

21. A solution phase sandwich hybridization assay for detecting the presence of a nucleic acid analyte in a sample, comprising:

(a) providing a solid support having capture probes thereon, capture extender molecules having a first segment C-1 capable of hybridizing to a nucleic acid sequence in the analyte and a second segment C-2 capable of hybridizing to a nucleic acid sequence in the capture probes, a first label extender molecule having a first segment L-1 capable of hybridizing to a nucleic acid sequence in the analyte and a second segment L-2 capable of hybridizing to a first amplification multimer, a second label extender molecule having a first segment L-1$a$ capable of hybridizing to a nucleic acid sequence in the analyte and a second segment L-2$a$ capable of hybridizing to a second amplification multimer, a first amplification multimer containing a nucleic acid sequence M-1 capable of hybridizing to L-2 and a plurality of identical oligonucleotide subunits containing nucleic acid sequences M-2 capable of hybridizing to label probes, a second amplification multimer containing a nucleic acid sequence M-1$a$ capable of hybridizing to L-2$a$ and a plurality of identical oligonucleotide subunits containing nucleic acid sequences M-2$a$ capable of hybridizing to label probes, and label probes capable of hybridizing to the amplification multimers and which, directly or indirectly, gives rise to a detectable signal;

(b) incubating the nucleic acid analyte under hybridization conditions with the capture extender molecules, label extender molecules and the capture probes on the solid support, simultaneously or sequentially in any order, to form a support-bound, first hybrid complex;

(c) thereafter optionally separating materials not bound to the solid support;

(d) contacting the support-bound, first hybrid complex under hybridization conditions with the amplification multimers, to produce a support-bound, second hybrid complex;

(e) thereafter optionally separating materials not bound to the solid support;

(f) contacting the support-bound, second hybrid complex with the label probes under hybridizing conditions, to produce a labeled, support-bound, third hybrid complex;

(g) thereafter separating materials not bound to the solid support;

(h) detecting the presence of label in the support-bound, third hybrid complex; and (i) correlating the presence of the label in the support-bound, third hybrid complex with the presence of the nucleic acid analyte in the sample, wherein the label probes contain a first nucleic acid segment which is capable of hybridizing to the first amplification multimer, and a second nucleic acid segment which is capable of hybridizing to the second amplification multimer, such that the support-bound, third hybrid complex is not formed unless the first and second amplification multimers are linked through the label probes.

22. A kit for detecting a nucleic acid analyte in a sample, comprising:

(a) a solid support having capture probes bound thereto;

(b) a first capture extender molecule capable of hybridizing to the capture probes and to predetermined segments of the nucleic acid analyte;

(c) a distinct second capture extender molecule capable of hybridizing to the capture probes and to segments of the nucleic acid analyte other than those to which the first capture extender molecule binds;

(d) label extender molecules capable of hybridizing to segments of the nucleic acid analyte other than those to which the first and second capture extender molecules bind;

(e) a label probe system comprising a nucleic acid sequence capable of hybridizing to the label extender molecules and which provide, directly or indirectly, a detectable signal, wherein the capture probes comprises a probe having a first capture extender binding sequence capable of hybridizing to the first capture extender molecule and a second capture extender binding sequence capable of hybridizing to the second capture extender molecule.

23. The kit of claim 22, wherein the label probe system comprises (f) an amplification multimer containing a nucleic acid sequence capable of hybridizing to the label extender molecules and a plurality of identical oligonucleotide subunits; and (g) label probes designed to hybridize to the identical oligonucleotide subunits and which provide, directly or indirectly, a detectable signal.

24. A kit for detecting a nucleic acid analyte in a sample, comprising:

(a) a solid support having capture probes bound thereto;

(b) capture extender molecules capable of hybridizing to the capture probes and to predetermined segments of the nucleic acid analyte;

(c) a first label extender molecule capable of hybridizing to predetermined segments of the nucleic acid analyte;

(d) a second label extender molecule capable of hybridizing to segments of the nucleic acid analyte other than those to which the first label extender molecule bind;

(e) an optional preamplifier probe capable of binding to the label extender molecules and to a plurality of amplification multimers;

(f) an amplification multimer containing a nucleic acid sequence capable of hybridizing to the label extender molecules or to the preamplifier probe, and a plurality of identical oligonucleotide subunits; and (g) label probes designed to hybridize to the identical oligonucleotide subunits and which provide, directly or indirectly, a detectable signal.

25. A kit for detecting a nucleic acid analyte in a sample, comprising:

(a) a solid support having capture probes bound thereto;

(b) capture extender molecules capable of hybridizing to the capture probes and to predetermined segments of the nucleic acid analyte;

(c) a first label extender molecule capable of hybridizing to predetermined segments of the nucleic acid analyte;

(d) a second label extender molecule capable of hybridizing to segments of the nucleic acid analyte other than those to which the first set of label extender molecules bind;

(e) a first amplification multimer containing (i) a nucleic acid sequence capable of hybridizing to the label extender molecule, and (ii) a plurality of identical oligonucleotide subunits;

(f) a second amplification multimer containing (i) a nucleic acid sequence capable of hybridizing to the label extender molecule, and (ii) a plurality of identical oligonucleotide subunits; and (g) label probes containing a first nucleic acid sequence capable of hybridizing with the oligonucleotide subunits of the first amplification multimer, and a second nucleic acid sequence capable of hybridizing with the oligonucleotide subunits of the second amplification multimer, and which provide, directly or indirectly, a detectable signal.

* * * * *